(12) United States Patent
Bryan

(10) Patent No.: US 8,894,832 B2
(45) Date of Patent: Nov. 25, 2014

(54) SAMPLING PLATE

(75) Inventor: Matthew Robert Bryan, Yorkshire (GB)

(73) Assignee: Jabil Circuit (Singapore) Pte, Ltd., St. Petersburg, FL (US)

( * ) Notice: Subject to any disclaimer, the term of this patent is extended or adjusted under 35 U.S.C. 154(b) by 0 days.

(21) Appl. No.: 13/637,813

(22) PCT Filed: Mar. 30, 2011

(86) PCT No.: PCT/GB2011/050654
§ 371 (c)(1),
(2), (4) Date: Sep. 27, 2012

(87) PCT Pub. No.: WO2011/124906
PCT Pub. Date: Oct. 13, 2011

(65) Prior Publication Data
US 2013/0020198 A1    Jan. 24, 2013

(30) Foreign Application Priority Data
Mar. 30, 2010 (GB) .................. 1005357.7

(51) Int. Cl.
G01N 27/327 (2006.01)
C12Q 1/00 (2006.01)
B01L 3/00 (2006.01)

(52) U.S. Cl.
CPC ........... C12Q 1/006 (2013.01); B01L 2300/027 (2013.01); B01L 2200/04 (2013.01); B01L 2200/12 (2013.01); B01L 2200/0642 (2013.01); B01L 2200/0684 (2013.01); B01L 3/502715 (2013.01); B01L 2300/0816 (2013.01); B01L 3/502723 (2013.01); B01L 2300/165 (2013.01); B01L 2300/0681 (2013.01); G01N 27/3272 (2013.01)
USPC .......................................... 204/415; 422/547

(58) Field of Classification Search
CPC .................... B01L 3/502715; G01N 27/3272
USPC .................................. 204/400, 415; 422/547
See application file for complete search history.

(56) References Cited

U.S. PATENT DOCUMENTS 4,618,475 A    10/1986   Wang
5,192,415 A    3/1993    Yoshioka et al.
(Continued)

FOREIGN PATENT DOCUMENTS

DE    19747875 A1    5/1999
EP     0170375 A2    2/1986
(Continued)

OTHER PUBLICATIONS

Patent Cooperation Treaty, International Search Report for Application No. PCT/GB2011/050654 dated Jul. 7, 2011, 3 pages.
(Continued)

Primary Examiner — J. Christopher Ball
(74) Attorney, Agent, or Firm — Volpe and Koenig, P.C.

(57) ABSTRACT

The present invention relates to a sampling plate. In particular the invention relates to a sampling plate for measuring certain selected properties of a liquid sample, such as the glucose levels in a blood sample. Sampling plates of the present invention have a sample zone (20) for receiving a liquid sample which is surrounded by an air porous body (4). The air porous body (4) acts to receive air from the sample zone (20) as it is displaced by an incoming liquid sample, thereby allowing efficient spreading of the liquid sample.

13 Claims, 9 Drawing Sheets

(56) References Cited

U.S. PATENT DOCUMENTS

| | | | |
|---|---|---|---|
| 5,264,103 A | 11/1993 | Yoshioka et al. |
| 5,304,468 A | 4/1994 | Phillips et al. |
| 5,341,805 A | 8/1994 | Stavridi et al. |
| 5,352,411 A | 10/1994 | Khuri |
| 5,391,272 A | 2/1995 | O'Daly et al. |
| 5,395,504 A | 3/1995 | Saurer et al. |
| 5,413,690 A | 5/1995 | Kost et al. |
| 5,413,761 A | 5/1995 | Dulaney |
| 5,563,042 A | 10/1996 | Phillips et al. |
| 5,658,444 A | 8/1997 | Black et al. |
| 5,708,247 A | 1/1998 | McAleer et al. |
| 5,843,691 A | 12/1998 | Douglas et al. |
| 5,843,692 A | 12/1998 | Phillips et al. |
| 5,951,836 A | 9/1999 | McAleer et al. |
| 5,997,817 A | 12/1999 | Crismore et al. |
| 6,066,243 A | 5/2000 | Anderson et al. |
| 6,066,847 A | 5/2000 | Rosenthal |
| 6,106,780 A | 8/2000 | Douglas et al. |
| 6,110,522 A | 8/2000 | Lepper, Jr. et al. |
| 6,241,862 B1 | 6/2001 | McAleer et al. |
| 6,254,736 B1 | 7/2001 | Earl et al. |
| 6,268,162 B1 | 7/2001 | Phillips et al. |
| 6,270,637 B1 | 8/2001 | Crismore et al. |
| 6,475,372 B1 | 11/2002 | Ohara et al. |
| 6,503,701 B1 | 1/2003 | Bauer |
| 6,525,330 B2 | 2/2003 | Paolini et al. |
| 6,541,216 B1 | 4/2003 | Wilsey et al. |
| 6,558,528 B1 | 5/2003 | Matzinger |
| 6,562,210 B1 | 5/2003 | Bhullar et al. |
| 6,562,625 B2 | 5/2003 | Modzelewski et al. |
| 6,592,815 B1 | 7/2003 | Zimmer |
| 6,603,987 B2 | 8/2003 | Whitson |
| 6,612,111 B1 | 9/2003 | Hodges et al. |
| 6,662,439 B1 | 12/2003 | Bhullar |
| 6,676,995 B2 | 1/2004 | Dick et al. |
| 6,689,265 B2 | 2/2004 | Heller et al. |
| 6,723,500 B2 | 4/2004 | Yu |
| 6,730,200 B1 | 5/2004 | Stewart et al. |
| 6,743,635 B2 | 6/2004 | Neel et al. |
| 6,746,960 B2 | 6/2004 | Goodman |
| 6,764,581 B1 | 7/2004 | Forrow et al. |
| 6,821,400 B2 | 11/2004 | Jaeger |
| 6,863,800 B2 | 3/2005 | Karinka et al. |
| 7,118,667 B2 | 10/2006 | Lee |
| 2002/0006355 A1 | 1/2002 | Whitson |
| 2002/0084196 A1 | 7/2002 | Liamos et al. |
| 2002/0100685 A1 | 8/2002 | Huang et al. |
| 2002/0125145 A1 | 9/2002 | Ohara et al. |
| 2002/0168290 A1 | 11/2002 | Yuzhakov et al. |
| 2002/0177788 A1 | 11/2002 | Hodges et al. |
| 2003/0028087 A1 | 2/2003 | Yuzhakov et al. |
| 2003/0028125 A1 | 2/2003 | Yuzhakov et al. |
| 2003/0036202 A1 | 2/2003 | Teodorcyzk et al. |
| 2003/0042150 A1 | 3/2003 | Ryu et al. |
| 2003/0068666 A1 | 4/2003 | Zweig |
| 2003/0094383 A1 | 5/2003 | Kermani |
| 2003/0096424 A1* | 5/2003 | Mao et al. ............... 436/169 |
| 2003/0099773 A1 | 5/2003 | Dick et al. |
| 2003/0104510 A1 | 6/2003 | Yu |
| 2003/0106809 A1 | 6/2003 | Kermani et al. |
| 2003/0133847 A1 | 7/2003 | Hagen et al. |
| 2003/0185705 A1 | 10/2003 | Otake |
| 2003/0185708 A1 | 10/2003 | Otake |
| 2003/0188446 A1 | 10/2003 | Pugh |
| 2003/0200644 A1 | 10/2003 | Matzinger |
| 2003/0212344 A1 | 11/2003 | Yuzhakov et al. |
| 2003/0212346 A1 | 11/2003 | Yuzhakov et al. |
| 2003/0212347 A1 | 11/2003 | Sohrab |
| 2003/0223906 A1 | 12/2003 | McAllister et al. |
| 2003/0224203 A1 | 12/2003 | Raychaudhuri et al. |
| 2004/0026243 A1 | 2/2004 | Davies et al. |
| 2004/0038411 A1 | 2/2004 | Hayter et al. |
| 2004/0096927 A1 | 5/2004 | Chittock et al. |
| 2004/0137141 A1 | 7/2004 | Dick et al. |
| 2004/0157275 A1 | 8/2004 | Marfurt |
| 2004/0186394 A1 | 9/2004 | Roe et al. |
| 2004/0214345 A1 | 10/2004 | Matzinger et al. |
| 2004/0217016 A1 | 11/2004 | Khan |
| 2004/0236250 A1 | 11/2004 | Hodges et al. |
| 2004/0251132 A1 | 12/2004 | Leach et al. |
| 2004/0256248 A1 | 12/2004 | Burke et al. |
| 2004/0259180 A1 | 12/2004 | Burke et al. |
| 2004/0260511 A1 | 12/2004 | Burke et al. |
| 2004/0265171 A1 | 12/2004 | Pugia et al. |
| 2004/0265172 A1 | 12/2004 | Pugia et al. |
| 2005/0004494 A1 | 1/2005 | Perez et al. |
| 2005/0008537 A1 | 1/2005 | Mosoiu et al. |
| 2005/0013731 A1 | 1/2005 | Burke et al. |
| 2005/0016844 A1 | 1/2005 | Burke et al. |
| 2005/0019212 A1 | 1/2005 | Bhullar et al. |
| 2005/0023136 A1 | 2/2005 | Leach et al. |
| 2005/0023137 A1 | 2/2005 | Bhullar et al. |
| 2005/0023152 A1 | 2/2005 | Surridge et al. |
| 2005/0023154 A1 | 2/2005 | Kermani et al. |
| 2005/0069892 A1 | 3/2005 | Iyengar et al. |
| 2005/0098433 A1 | 5/2005 | Gundel |
| 2005/0103624 A1 | 5/2005 | Bhullar et al. |
| 2005/0109618 A1 | 5/2005 | Davies |
| 2005/0109637 A1 | 5/2005 | Iyengar et al. |
| 2005/0113717 A1 | 5/2005 | Matzinger et al. |
| 2005/0114062 A1 | 5/2005 | Davies et al. |
| 2005/0118062 A1 | 6/2005 | Otake |
| 2005/0133368 A1 | 6/2005 | Davies et al. |
| 2005/0136501 A1 | 6/2005 | Kuriger |
| 2005/0196747 A1 | 9/2005 | Stiene |
| 2006/0078986 A1 | 4/2006 | Ly et al. |
| 2006/0226985 A1 | 10/2006 | Goodnow et al. |
| 2006/0243591 A1 | 11/2006 | Plotkin et al. |
| 2006/0246214 A1 | 11/2006 | Plotkin et al. |
| 2006/0260940 A1 | 11/2006 | McAleer et al. |
| 2007/0281321 A1 | 12/2007 | Nagale et al. |
| 2008/0073207 A1 | 3/2008 | Teodorczyk et al. |
| 2008/0297169 A1 | 12/2008 | Greenquist et al. |
| 2009/0130719 A1 | 5/2009 | Handique |
| 2010/0089775 A1 | 4/2010 | Chen et al. |
| 2010/0219084 A1 | 9/2010 | Blythe et al. |
| 2011/0168575 A1 | 7/2011 | Lica et al. |
| 2011/0241694 A1 | 10/2011 | Burke et al. |
| 2012/0011705 A1 | 1/2012 | DeNuzzio et al. |

FOREIGN PATENT DOCUMENTS

| | | | |
|---|---|---|---|
| EP | 0787984 A1 | 8/1997 |
| EP | 1111378 A2 | 6/2001 |
| EP | 1304570 A1 | 4/2003 |
| EP | 1357194 A2 | 4/2003 |
| EP | 1421899 A1 | 5/2004 |
| EP | 1422523 A1 | 5/2004 |
| EP | 1723412 A2 | 11/2006 |
| EP | 1764030 A1 | 3/2007 |
| GB | 2463914 A | 3/2010 |
| GB | 2465842 A | 9/2010 |
| JP | 06288964 A2 | 10/1994 |
| WO | 9946045 A1 | 9/1999 |
| WO | 0175433 A2 | 10/2001 |
| WO | 03094713 A1 | 11/2003 |
| WO | 2005047877 A1 | 5/2005 |
| WO | 2005079664 A1 | 9/2005 |
| WO | 2006015615 A1 | 2/2006 |
| WO | 2006116616 A2 | 11/2006 |
| WO | 2007076940 A1 | 7/2007 |
| WO | 2008029110 A2 | 3/2008 |
| WO | 2008134587 A1 | 11/2008 |
| WO | 2011121352 A1 | 10/2011 |
| WO | 2011124906 A1 | 10/2011 |

OTHER PUBLICATIONS he State Intellectual Property Office of the People's Republic of China, the First Office Action for the National Phase of the PCT Application for CN Application No. 200980147833.8 dated Mar. 27, 2013, 16 pages.

Landre, International Application No. PCT/GB2011/050654, International Search Report, Jul. 18, 2011, 3 pages.

(56) References Cited

OTHER PUBLICATIONS

Nickitas-Etienne, International Application No. PCT/GB2011/050654, International Preliminary Report on Patentability, Oct. 2, 2012, 5 pages.

Tucker, Application No. GB0817842.8, Search Report under Section 17, Dec. 15, 2008, 2 pages.

Pidgeon, Application No. GB0817842.8, Response to Examination Letter, Mar. 21, 2012, 26 pages.

Cole, Application No. GB 1205054.8, Combined Search and Examination Report under Sections 17 & 18(3), dated Apr. 19, 2012, 4 pages.

Cole, Application No. GB 1205054.8, Search Report under Section 17, dated Apr. 18, 2012, 2 pages.

Patent Cooperation Treaty, PCT International Search Report and Written Opinion of the International Searching Authority for Application No. PCT/GB2009/051225 dated Jan. 1, 2010, 8 pages.

Kessel, U.S. Appl. No. 13/121,509, Office Action Communication, Sep. 25, 2012, 13 pages.

Kessel, Office Action Communication for U.S. Appl. No. 13/121,509 dated May 22, 2013, 25 pages.

* cited by examiner

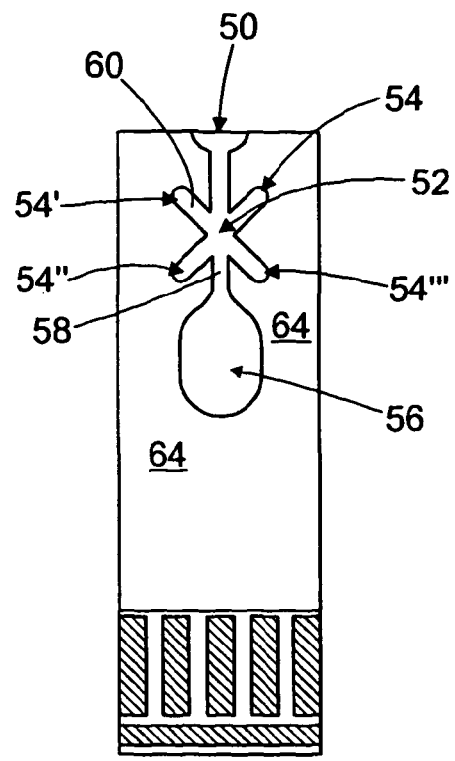
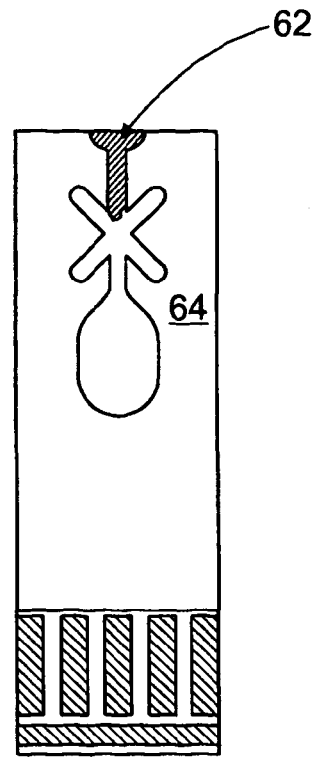
Fig. 3a
Fig. 3b
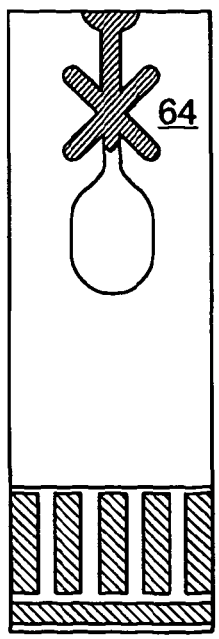
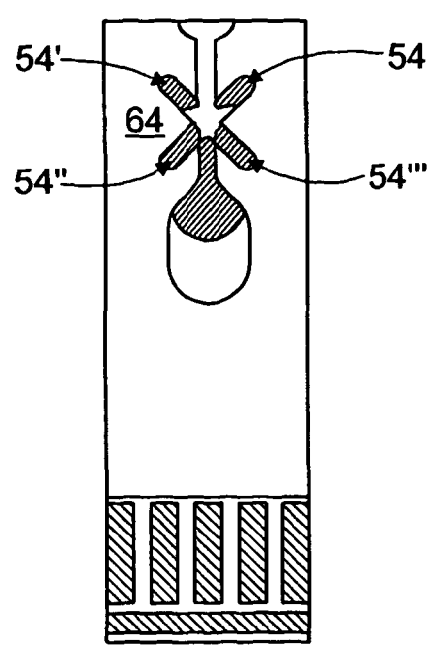
Fig. 3c
Fig. 3d

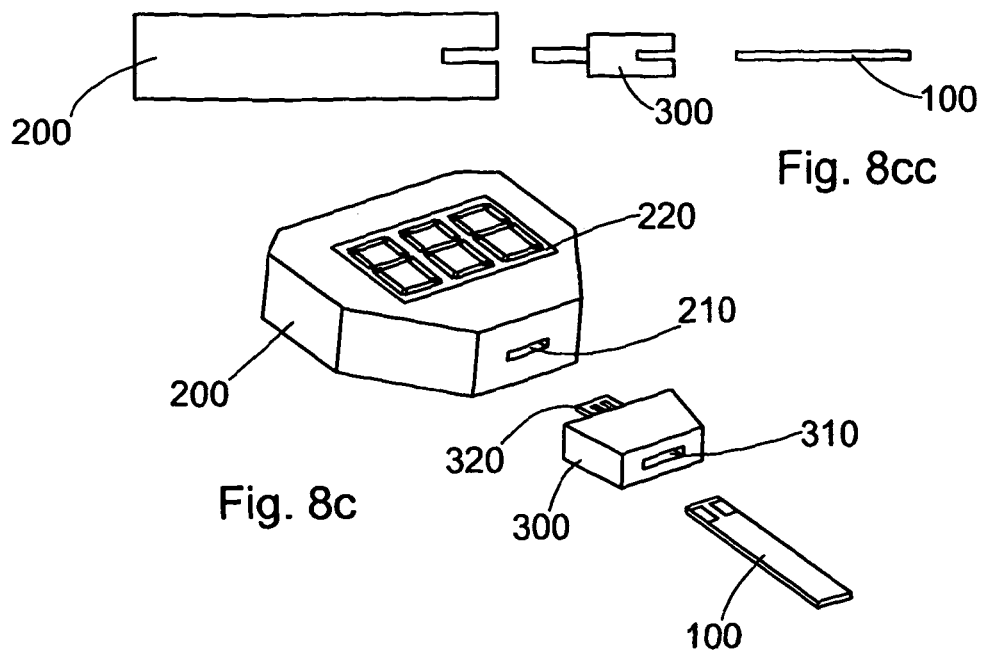
Fig. 8cc
Fig. 8c
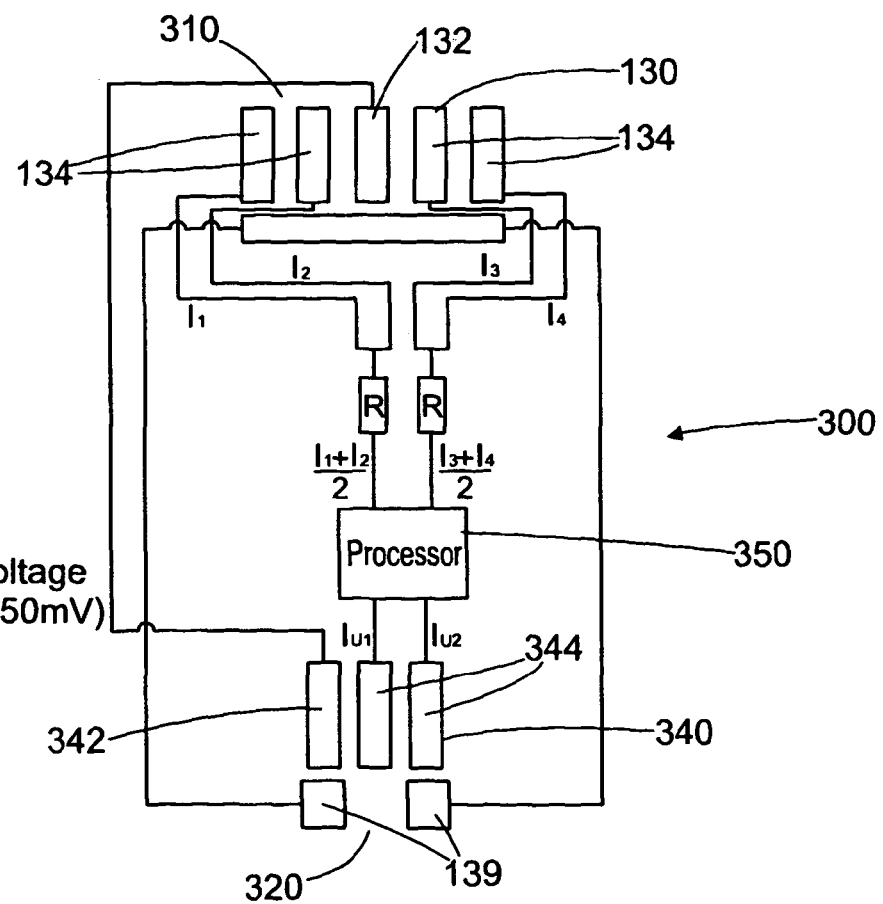
Fig. 8d

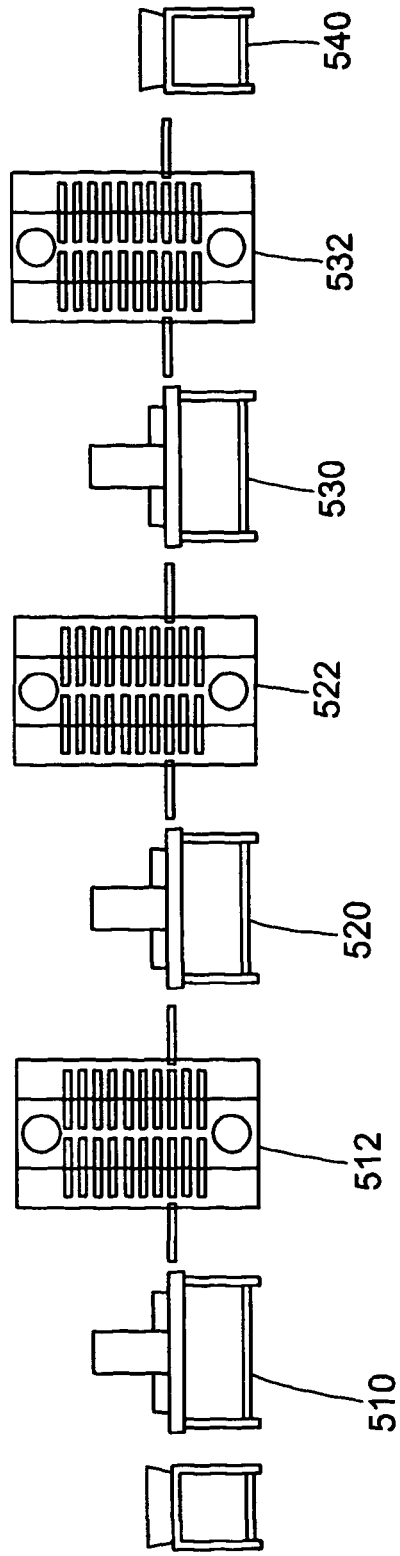
Fig. 11
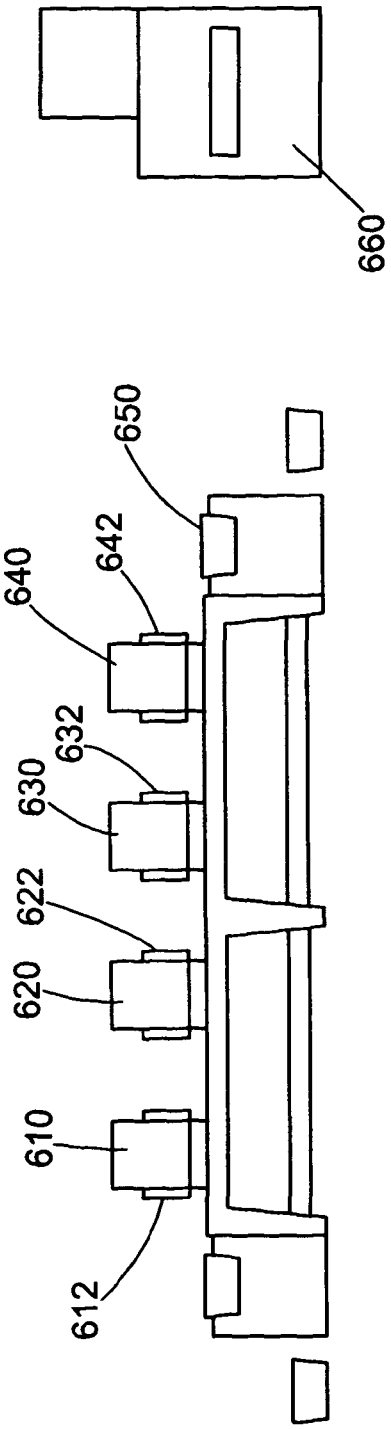
Fig. 12a
Fig. 12

SAMPLING PLATE

INTRODUCTION

The present invention relates to a sampling plate. In particular the invention relates to a sampling plate for measuring certain selected properties of a liquid sample, such as the glucose levels in a blood sample.

INTRODUCTION TO THE BACKGROUND ART

There is a widespread need for sampling plates such as those which, when used in conjunction with a measurement device, enable a diabetes patient to know their blood sugar levels—i.e. the concentration of glucose in their blood.

Traditional sampling plates function by receiving a spotted blood sample and directing at least some of the blood to a testing zone. The testing zone typically takes the form of a recess or well containing a quantity of glucose oxidase which chemically reacts with the blood to an extent and at a rate determined by the glucose concentration in the blood. The testing zone is typically furnished with a pair of electrode terminals which are conveniently bridged by the reaction mixture of the blood and glucose oxidase so as to allow for electrochemical readings by a corresponding measurement device. The electrochemical readings then provide an indication of blood glucose levels.

A problem with such traditional sampling plates is that blood spreading in and to the testing zone is often slow and/or non-uniform. For instance, blood spreading is often biased in the direction of an initial blood flow courtesy of surface tension. Sometimes a blood sample will not spread throughout the testing zone, and consequently measurements may be inaccurate or unreliable. This is a particular problem for sampling plates having a larger loading port to assist the less dextrous, such as the elderly or infirm.

It is an object of the present invention to provide an improved sampling plate.

SUMMARY OF THE INVENTION

According to a first aspect of the present invention there is provided a sampling plate, comprising:
a sample zone for receiving a liquid sample; and
an air porous body which is in fluid communication with the sample zone;
wherein the air porous body is arranged to receive air displaced from the sample zone as the liquid sample is received into the sample zone.

Herein, a "sampling plate" may mean any surface capable of receiving a liquid sample in a sample zone. Preferably, however, the sampling plate is portable. Suitably the sampling plate may cover an area less than $1 m^2$, preferably less than $50 cm^2$, more preferably less than $10 cm^2$ and most preferably less than $5 cm^2$. The sampling plate may cover an area less than $500 mm^2$—for instance $350 mm^2$ where the sampling plate is 10 mm wide by 35 mm long. Suitably the sampling plate may be rectangular. The sampling plate may be a strip, and may be a flexible strip. Preferably, however, the sampling plate is an individual plate, preferably a rigid sampling plate. The thickness of the sampling plate is preferably less than 1 cm, preferably less than 1 mm, more preferably less than 0.5 mm, most preferably less than 0.25 mm.

The sampling plate is preferably compatible with a measurement device. For example, the measurement device is preferably operable to communicate with the sampling plate to measure one or more selected properties of any of the at least two samples. Preferably the sampling plate may be inserted into the measurement device to allow measurements to be taken. The measurement device is preferably in accordance with that described in co-pending application PCT/GB2009/051225 filed on 21 Sep. 2009 by the present applicants. This co-pending application is hereby incorporated by reference.

"In fluid communication with" may mean interfacing, where "interfacing" means sharing a common boundary. Preferably "in fluid communication with" refers to where the air porous body is adjacent to the sample zone. The air porous body may define a floor of the sample zone and/or wall(s) of the sample zone. The air porous body may surround the sample zone. Preferably the air porous body defines the sample zone, or defines an outer boundary of the sample zone. Preferably the air porous body defines the perimeter of the sample zone or at least part of the perimeter of the sample zone. Preferably the air porous body is external to the sample zone itself. Preferably the sample zone is free of air porous body.

Preferably the air porous body is arranged to receive displaced air as the liquid sample approaches the air porous body. Preferably the air porous body is arranged to receive air displaced in the same direction as the liquid sample travels (or spreads) into the sample zone. Preferably the air porous body is arranged to receive a side-ways displacement of air as the liquid sample approaches the air porous body in a side-ways manner. Preferably the sample zone is arranged to prevent back flow of the liquid sample.

An advantage of the present invention is that the air porous body helps the liquid sample to flow into the sample zone with minimal air resistance, by providing a means by which air can be directly displaced—preferably in the same direction as the liquid sample enters the sample zone. This permits the liquid sample to enter the sample zone at a faster rate. In contrast, where such an air porous body is absent, air resistance retards the flow of the liquid sample into the sample zone.

Another advantage of the present invention is that the air porous body helps the liquid sample to spread uniformly throughout the sample zone, thus giving greater sampling consistency and consequently more accurate measurements. In contrast, where the air porous body is absent, air resistance affects the fluid dynamics of the liquid sample by discouraging spreading (air resistance from all sides) and instead encouraging the liquid sample to remain collectively associated as a bulk (aided by surface tension). As such the liquid sample tends to flow as a bulk in a single direction since in this way the bulk overcomes air resistance in that particular direction.

Another advantage is that formation of air-pockets is alleviated, which again allows for better spreading and more accurate measurements.

The liquid sample is preferably hydrophilic, more preferably aqueous-based, and most preferably blood. In this case, blood glucose levels of a diabetic patient may be measured.

The air porous body is preferably substantially impermeable to the liquid sample. The air porous body is preferably substantially impermeable to water. The air porous body is preferably substantially impermeable to an aqueous liquid sample, and most preferably substantially impermeable to blood.

The air porous body is preferably impermeable to water (at standard temperature and pressure) to the extent that the air porous body remains visibly wet for at least 15 seconds, preferably at least 30 seconds, more preferably at least 1 minute, most preferably at least 10 minutes, after wetting a portion of the air porous body with the smallest drop of water required to impart visible wetness.

The air porous body is preferably suitable for containing 100% of the liquid sample for at least 15 seconds, more preferably for at least 1 minute, and most preferably at least 10 minutes. The air porous body is preferably totally impermeable to the liquid sample, water, an aqueous liquid sample, or a blood sample. Such impermeability is preferably imparted by the hydrophobicity of the air porous body rather than the small size of its pores. Most preferably the air porous body is arranged to contain the liquid sample in the sample zone. Preferably the air porous body is arranged to hold the liquid sample, preferably an aqueous liquid sample, and more preferably blood, within the sample zone.

Preferably the perimeter of the sample zone comprises a wall. Preferably the perimeter (or wall) of the sample comprises at least some air porous body. Preferably at least 50% of the perimeter comprises air porous body, preferably at least 70%, more preferably at least 90%, and most preferably at least 95% of the perimeter comprises air porous body. Preferably the perimeter comprises substantially 100% air porous body. The air porous body is preferably located substantially around the perimeter of the sample zone. Preferably a floor of the sample zone is free of air porous body. Preferably the sample zone is free of a roof. Where the sample zone comprises a roof, the roof is preferably free of air porous body.

The air porous body preferably comprises hydrophobic material. Preferably the air porous body comprises at least 50 wt %, more preferably at least 70 wt %, and most preferably at least 90 wt % hydrophobic material. In some embodiments the air porous body may comprise a mixture of hydrophobic and hydrophilic material. Preferably the air porous body is hydrophobic overall (i.e. has a net hydrophobicity). Hydrophobicity may be measured by considering techniques well known in the art. In general, the air porous body exhibits the requisite net hydrophobicity where a drop of water rolls off the surface of the air porous body when such a surface is inclined at least 30° from horizontal, preferably at least 20° from horizontal, and most preferably at least 10° from horizontal.

The porosity of a porous material generally describes a fraction of void space (capable of containing fluids) in the porous material, and may be expressed as:

$$\Phi = V_v/V_T;$$

where $V_v$ is the volume of void space, and $V_T$ is the total volume of material including void space. There are a number of ways of measuring porosity, including:

Direct methods—determining the bulk volume of the porous material and then determining the volume of skeletal material with no pores (pore volume=total volume−skeletal material volume);

Optical methods—determining the area of the material versus the area of the pores visible under a microscope. This method is accurate for materials with random structure since areal porosity and volumetric porosity is then the same.

Imbibition methods—immersing the porous material, under vacuum, in a fluid the preferentially wets the pores. In this case a non-hydrophilic fluid would be preferred which does not dissolve the air porous body. Those skilled in the art would readily select a suitable solvent. (pore volume=total volume of fluid−volume of fluid left after soaking).

Fluid evaporation method (pore volume is a function of: weight of a porous material saturated with fluid−weight of dried air porous body).

Many other methods are also known in the art.

The air porous body preferably has a porosity of at least 0.001, preferably at least 0.01, more preferably at least 0.1, and most preferably at least 0.2. The air porous body preferably has a porosity of at most 0.95, preferably at most 0.90, more preferably at most 0.8, and most preferably at most 0.7. The most preferably porosity is between 0.3 and 0.4. A porosity lower than the preferred minimum impedes air displacement. A porosity above the preferred maximum risks the air porous body becoming moderately permeable to the liquid sample, particularly water or blood.

The air porous body preferably has an average pore size between 10 and 300 microns, preferably between 50 and 200 microns, and most preferably between 100 and 150 microns.

Pores of the air porous body are preferably free from blockage by a pore blocking substance. For instance, the pore blocking substance may include an adhesive, especially an adhesive for adhering the air porous body to the sampling plate. The air porous body must, of course, be porous when incorporated into the sampling plate. The extent of pore blocking is the extent to which the void space of the air porous body (i.e. the space of the pores) is occupied by the pore blocking material, as measurable in accordance with the above techniques or others well known in the art. Preferably the pores of the air porous body are less than 70% blocked, preferably less than 50% blocked, more preferably less than 30% blocked, and most preferably less than 10% blocked.

The air porous body preferably comprises an air porous mesh, which again is preferably hydrophobic overall. Such an air porous mesh preferably comprises polyether ether ketone (PEEK), polypropylene (PP), polyester (PET), polyvinylidene fluoride (PVDF), ethylene chlorotrifluoroethylene (ECTFE), ethylene co-tetrafluoroethylene (ETFE), nylon (polyamide), or fluorinated ethylene-propylene (FEP). The air porous mesh preferably comprises polyester (PET). Most preferably the air porous mesh comprises Sefar 07-120 34. Such materials are the most suitable for being adhered to a sampling plate whilst minimising pore blockage which would otherwise undesirably reduce air porosity.

The thread diameter of the mesh is preferably between 10 and 300 microns, more preferably between 50 and 200 microns, and most preferably between 70 and 100 microns.

The air porous body is preferably a porous layer of the sampling plate. The porous layer preferably has a thickness of between 0.01 mm and 3 mm, more preferably between 0.1 mm and 1 mm, most preferably 0.1 mm to 0.2 mm. The porous layer is preferably adhered to the sampling plate, preferably by an adhesive. Preferably the adhesive comprises synthetic rubber adhesive. The adhesive preferably covers 1 to 20 g/m², more preferably 5 to 15 g/m², most preferably 10 g/m² of the surface of the porous layer. The adhesive may be comprised of double-sided adhesive tape, wherein the preferred coverage of adhesive as stated above refers to adhesive lying between the adhesive tape and the porous layer. This ensures that pore blockage of the air porous body is kept to a minimum, especially when the adhesive is used in combination with one of the preferred air porous mesh materials. The porous layer preferably comprises an empty portion (or hole) arranged to receive and contain the liquid sample. The outer limits of the empty portion preferably defines the perimeter of the sample zone.

The sample zone preferably comprises a testing zone, possibly only a single testing zone. Preferably, however, the sample zone comprises at least two discrete testing zones.

The presence of the air porous body is particularly advantageous where there is more than one testing zone since such technology allows the liquid sample to spread into each testing zone, rather than tending to fall towards just one. The sample zone is preferably arranged, in use, to separate the liquid sample into at least two discrete samples, where preferably each discrete sample occupies a respective testing zone. By "discrete" it is meant that samples are fully separated from each other. In particular, they are not linked together by a portion of the liquid sample which may, for instance, otherwise remain on a fluid path between the at least two discrete samples. Discrete samples, rather than samples which overlap, allows for greater accuracy in measurements. The invention also has the advantage that each of the at least two discrete samples is exposed to only one testing zone, thereby avoiding contamination or interference by another testing zone, which may otherwise lead to inaccurate measurements. By "to separate the liquid sample into at least two discrete samples" it is meant that the sample zone actively separates the liquid sample into and maintains separation of the discrete samples.

The sampling plate is preferably operable to communicate with a measurement device such that one or more selected properties of any of the at least two discrete samples is measureable. The invention allows multiple measurements to be taken in respect of a plurality of discrete samples. For example, one sample may be used to determine one selected property (e.g. physiological condition); another sample may be used to determine another selected property. The measurements may pertain to the same property or different properties, thus allowing for detailed analysis of a liquid sample, such as a patient's blood, using a single sampling plate.

Preferably the sampling plate is operable to take an electrochemical measurement in respect of each sample. The sample zone may have three or more testing zones, preferably from three to five testing zones, most preferably four testing zones. The presence of multiple testing zones and samples allows for determination and/or quantification of different metabolites, assessment of different physiological conditions, averaging of measurement results, and validation of measurement results.

The sample zone may comprise a separation means for separating the liquid sample into at least two discrete samples, such that each sample occupies a respective testing zone. For instance, the separation means may comprise a hydrophobic zone or boundary (hereinafter hydrophobic boundary) which, in use, lies between the at least two testing zones. A preferred hydrophobic material is flexographic ink, preferably doped with at least one component which increases hydrophobicity, e.g. a detergent. Most preferably the hydrophobic material comprises a hydrophobic acrylic resin, a silicone antifoaming agent, micronized wax, and fumed silica (as a filler). This is advantageous as the hydrophobic boundary separates samples, and/or assists in the separation of the liquid sample into two or more discrete samples. The separation means may comprise a primary hydrophobic zone located towards the centre of the sample zone or towards a central region lying between all the respective testing zones. The primary hydrophobic zone may be arranged to first receive the liquid sample before distributing the liquid sample amongst the respective testing zones. The primary hydrophobic region may be a raised portion of the sample zone (i.e. located at a different depth within the sampling plate than a floor of each respective testing zone), preferably allowing the liquid sample to fall towards into and into the respective testing zones by virtue of gravity (for instance, when the sampling plate is held with the sample zone facing upwards). Preferably hydrophobic boundaries emanate from the primary hydrophobic zone, and preferably define divisions between each testing zone.

The sample zone may comprise a hydrophilic floor or floors for containing the liquid sample. Each of the at least two testing zones preferably comprises a hydrophilic portion, which is arranged to receive one of the at least two discrete samples. A preferred hydrophilic material is flexographic ink, preferably doped with at least one component which increases hydrophilicity. The hydrophilic material preferably comprises a water-based acrylic polymer and a surfactant (preferably either TWEEN 20 or TWEEN 80). Surface tension tends to keep each sample in its own testing zone.

Each testing zone preferably comprises a well, where each well is arranged to receive one of the at least two discrete samples. The well may be circular or non-circular (that is at the mouth), and possibly substantially square shaped (i.e. at the mouth). Preferably the well has sides where the sides are substantially sloped. Preferably the sides connect to a base of the well and to a top sheet (in which the well is formed) in a smooth or continuous manner, without any discontinuities. The well may have a surface area of between 2.5 and 4 $mm^2$ and a depth of 200-300 μm. Each well may comprise the abovementioned hydrophilic portion. A well helps to keep the samples discrete, and also provides a three dimensional target for dosing inks thereinto (see below). This improves the manufacturing process.

The wells are preferably rounded, and preferably circular (that is at the mouth). Preferably the wells are free of corners, preferably free of sharp corners. Preferably the wells comprise a continuous surface, preferably a curved surface. Most preferably the wells are dimples, preferably hemispherical dimples. The hemispherical wells may have a depth between 100 μm and 200 μm.

All the testing zones may, in use, be employed for providing measurements of a sample contained therein. However, one or more of the at least two testing zones may serve an alternative purpose, such as to collect excess liquid sample to avoid the other testing zones from becoming overfilled.

The sample zone may therefore help separate the liquid substance into discrete samples by virtue of its shape. This may include paths. This may also include troughs, recesses, etc., herein broadly referred to as wells. The sample zone may also help separate the liquid substance by virtue of chemical means. For instance, the sample zone may comprise certain hydrophobic region(s) and/or hydrophobic region(s). Preferably the sample zone helps to separate the liquid substance into discrete samples by virtue of both its shape and the chemical means.

At least one testing zone preferably comprises a laid-down material, which in the medical testing field is conventionally called an "ink" (this term is used hereinafter). The ink may have a pigment, but not necessarily. Preferably the ink comprises a test material, so as to be an "active" ink. Preferably the test material is selected to be chemically reactive with at least one component of the liquid sample. This reactivity may provide the basis for measurements of a selected property of the liquid substance. The test material is preferably bound to the testing zone, so as not to flow during normal handling of the sampling plate. The test material is preferably dried on to the testing zone, and may be a dried coating, gel or paste. Preferably it is formed from a liquid precursor, preferably a solution of the test material. The test material within the ink is preferably selected to be chemically reactive with glucose. However, the test material may also be selected to be reactive with another component of the liquid sample, such as ketones.

The test material preferably comprises an enzyme, preferably either glucose oxidase or glucose dehydrogenase.

Preferably more than one of at least two testing zones comprises an ink. Each ink may be different or comprise a different test material. Each different ink may react with the same component, so as to provide measurements which are self-calibrating. Alternatively each different ink may react with a different component of the liquid sample, enabling measurement of a plurality of selected properties. Measurement of a plurality of selected properties allows assessment and/or monitoring of a plurality of different illnesses, conditions, and/or medical states (analyte levels/concentration). It also allows assessment or monitoring of such as recreational drug use, or alcohol abuse. In particular it allows assessment of the use of a plurality of recreational drugs simultaneously.

Preferably at least one testing zone comprises a "mediator" ink. The mediator ink is conductive when in solution or mixed with a liquid sample such as blood. This increases the sensitivity of the measurements. The same at least one testing zone preferably further comprises either an active ink or a passive ink. The active ink comprises a test material, whereas the passive ink is the same as the active ink but without the test material. The mediator ink and active or passive ink may be substantially mixed with each other, rather than being layered. This can be achieved by pre-mixing the inks before laying them down in the at least one testing zone.

The sampling plate preferably comprises at least one pair of electrodes arranged to permit an electrochemical measurement to be taken in respect of the liquid sample. The sampling plate preferably comprises at least one pair of electrodes connectable to electrical terminals within the measurement device. A pair of electrodes generally consists of an anode/cathode pair. Preferably at least one and preferably each testing zone (or well) contains a pair of electrodes. The at least one pair of electrodes is preferably bridged, in use, by the liquid sample in a testing zone. In use, that testing zone preferable contains an electrolyte, where the electrolyte is preferably one of the at least two discrete samples, and is more preferably the reaction product of one of the at least two samples with an ink. The measurement device may suitably communicate with the sampling plate by applying a potential difference across the at least one pair of electrodes. Such communication preferably provides measurements in respect of the electrolyte to determine certain one or more selected properties of the liquid sample. Such an electrochemical measurement technique is typically more accurate than other sample measurement techniques available in the field, such as optical measurements. Preferably, after loading the liquid sample, the system requires a period of time, preferably from 3 to 15 seconds, before the result is made available.

A pair of electrodes per testing zone does not exclude an embodiment where all or some testing zones have a single common electrode, whether a cathode or an anode. Such a common electrode has a plurality of termini (electrolyte contacts) adjacent to or in each testing zone. In this case each testing zone associated with the common electrode preferably has its own individual opposite electrode, whether an anode or cathode. In fact, a single common electrode arrangement is preferred owing to ease of manufacture of both the sampling plate and the corresponding measurement device.

The electrodes are preferably printed, most preferably flexographically printed electrodes. The printed electrodes preferably comprise an ink. Said ink preferably comprises conductive particulates such as carbon and/or graphite. The ink may be printed to a specific design.

Preferably each testing zone is electrically isolated. Preferably a space between the electrodes comprises insulating material, preferably printed insulation material, most preferably flexographically printed insulation material. This helps prevent signal interference between electrodes. The insulation material preferably comprises an ink that is free of conductive particulates or conductive ingredients, and is preferably printed to a specific design that electrically isolates the conductive electrodes from each other.

The electrolyte is preferably producible by a chemical reaction between at least one component of the liquid sample and the ink. Selected properties may be measurable from an electric current measurement. A constant potential difference, preferably between 100 and 1000 millivolts (mV), through the at least one pair of electrodes and across a corresponding testing zone may give rise to an electric current, which current is dependent on the selected property, e.g. glucose concentration. In some embodiments it is believed that the anode and cathode actually cause a chemical reaction. In other embodiments the anode and cathode are believed not to cause a chemical reaction.

The sampling plate preferably comprises a loading port. In one embodiment the loading port is arranged on a top face of the sampling plate. Such a top-fill arrangement is readily accessible for loading a liquid sample, especially for those with reduced dexterity, such as the elderly or infirm. Furthermore, such sampling plates may be thin in profile. Preferably a top-fill loading port is arranged directly above or over the sample zone. This means that the liquid substance, once loaded at the loading port, is delivered straight to the sample zone, and this may be assisted by gravity. Such an arrangement also allows gravity to assist or cause splitting and/or delivery of the liquid sample into the at least two testing zones. This helps to ensure that each sample forms within its respective testing zone as a fully discrete sample, rather than being linked to other samples by liquid substance remaining along a fluid path.

In another embodiment the loading port is arranged at one end of the sampling plate. This has its own advantages, over a top-fill arrangement. Firstly, it is a traditional approach, and users are familiar with it. This is of significant benefit particularly in relation to older patients who may not adapt readily to new blood delivery formats. Secondly many patients may use it more accurately. It can be difficult to "aim" well at a top-fill loading port.

The loading port is preferably circular or rectangular. Preferably the loading port has an area of between 5 and 10 $mm^2$, more preferably between 6 and 8 $mm^2$. Preferably the loading port comprises an opening in a covering tape. Preferably the covering tape is a hydrophilic film. Preferably the hydrophilic film spreads at least some of the liquid sample on its underside (i.e. inside the sampling plate) when in use.

The sampling plate may comprise a spreading means for assisting distribution of the samples to their respective testing zones. The spreading means may comprise the hydrophilic film. In some embodiments, the spreading means may comprise a mesh spreading means over the sample zone. Such a mesh spreading means may permit the liquid substance to pass therethrough into the at least two testing zones. The mesh spreading means helps to spread the liquid substance uniformly over the sampling zone as a whole, and particularly helps spread the liquid substance uniformly over the two or more testing zones.

The mesh spreading means may comprise a mixture of mesh hydrophobic and mesh hydrophilic materials. The mesh spreading means is preferably cross-hatched. The mesh spreading means may comprise parallel strands of hydrophobic material and at least partially orthogonal but parallel strands of hydrophilic material. Alternatively, parallel strands may be alternately hydrophobic and hydrophilic. Provision of hydrophilic material in the mesh spreading means helps to spread the liquid sample. Provision of hydrophobic material in the mesh spreading means helps repel the liquid sample into the testing zones. The mesh spreading means may therefore have a top face coated with hydrophilic material, and a bottom face coated with hydrophobic material.

Where a mesh spreading means is present, it is preferably disposed between the loading port and the sample zone.

Preferably, however, the sample zone is free of mesh spreading means. Preferably a region over the sample zone is free of mesh spreading means. Preferably a region over the sample zone is free of mesh. The sample zone is preferably arranged to spread the liquid sample, preferably unaided by capillary action.

The sampling plate may comprise an information tag, readable by an information tag reader associated with the measurement device. The information tag may include, but is not limited to, product authentication information. This may prevent harmful circulation/use of counterfeit sampling plates. The information tag preferably comprises a performance indicator, arranged to communicate with the measurement device. The measurement device therefore preferably comprises a performance indicator reader (preferably comprised of the information tag reader) to read the performance indicator. Preferably the performance indicator is for automatic performance band calibration. This avoids the need for a user to input a performance band into the measurement device before taking measurements. The performance indicator is preferably a performance band transmitter arranged to communicate with a performance band receiver comprised of the measurement device. Preferably the transmitter is a radio frequency transmitter such as an RFID tag (radio-frequency identification tag).

The information tag may contain batch information, particularly batch information pertaining to the production of the specific sampling plate. Such batch information may allow for total traceability of the sampling plate by reference to batch records. Such batch records may include information regarding the sampling plate's constituent parts, and materials, along with process control and operator efficiency during the sampling plate's production. Therefore the batch information may be a simple master batch number which refers to relevant batch records. Therefore, a faulty sampling plate may be interrogated to provide a reference to all quality records associated with its production. In this case, the information tag may be read by the information tag reader of the measurement device, as described above. However, the information tag may also be read by an information tag reader linked to a computer, which may include the measurement device being linked to a computer.

The sample measurement system may further comprise an adaptor to allow the measurement device to communicate with the sampling plate. The adaptor is preferably in accordance with that described in co-pending application PCT/GB2009/051225 filed on 21 Sep. 2009 by the present applicants. The adaptor may allow a sampling plate of the present invention to be adapted for use with a traditional measurement device. In this case such a traditional measurement device may serve only as a display device to display measurement results, which measurement results are generated by the adaptor itself. In such a case, the adaptor itself may comprise an information tag reader, preferably comprising a performance indicator reader. The performance indicator reader may receive performance band information from the performance indicator of the sampling plate, and use such information to calibrate measurement results before sending the results to be displayed on the traditional measurement device. Compatibility with old measurement devices may be important for a smooth transition to using the technology of the present invention, as the measurement devices are more expensive than the sampling plates. Furthermore, patients often prefer to keep a measurement device with which they are already familiar.

Alternatively, the adaptor may also allow traditional sampling plates to be used with the measurement device of the present invention. In this case, the adaptor may itself comprise an information tag which communicates information about the traditional sampling plate to the information tag reader.

In accordance with a second aspect of the present invention there is provided a measurement device as described in the first aspect. The measurement device is preferably arranged to receive the sampling plate of either the first or second aspect without adaptation, for instance with an adaptor. The measurement device may be handheld.

In accordance with a third aspect of the present invention there is provided an adaptor as described in the first aspect. The adaptor may be connectable between the measurement device and any other sampling plate, or the sampling plate and any measurement device. The adaptor may comprise electrical connectors (contacts) to connect the at least one pair of electrodes of the sampling plate to a power source or terminals within the measurement device.

Where the adaptor is connectable between the sampling plate of the present invention and any measurement device, the adaptor may comprise a signal manipulator. The signal manipulator is preferably arranged in use to manipulate one or more sampling plate output signals to provide one or more adaptor output signals, which adaptor output signals are compatible with the measurement device and usable to measure one or more selected properties of any of the at least two samples of the sampling plate. Preferably none of the one or more sampling plate output signals are compatible with the measurement device. Preferably the number of adaptor output signals is less than the number of sampling plate output signals. Moreover, the signal manipulator may also manipulate one or more signals in the opposite direction, i.e. between the measurement device and the sampling plate.

The adaptor may comprise a processor. Preferably the processor is a computer processor, preferably comprising a microchip. The processor may be comprised of the signal manipulator. The processor preferably manipulates the signals before they are fed into the measurement device.

The adaptor of the present invention allows a user to keep and continue using an old measurement device whilst still benefiting from at least some of the advantages of the sampling plate of the present invention.

In accordance with a fourth aspect of the present invention there is provided an adaptor for connecting any sampling plate (not necessarily as defined in the first aspect) to any measurement device (not necessarily as defined in the first aspect). The adaptor may comprise a processor for managing two-way communication between the sampling plate and measurement device, which may otherwise be incompatible.

According to a fifth aspect of the present invention there is provided a method of testing a medical condition comprising:
 a) loading a liquid substance from the body to a sampling plate of the first aspect;
 b) operating a measurement device to communicate with the sampling plate to measure one or more selected properties of the liquid substance.

The method preferably comprises testing diabetes. The method may comprise testing for the presence of one or more recreation drugs, and may include tests for alcohol.

The method may comprise testing cardiac conditions, such as elevated adrenalin levels. Potentially any condition which causes a change in concentration of a component in the blood (indicative chemistry) may be tested for.

According to a sixth aspect of the present invention there is provided a diagnostic kit for testing a medical condition, comprising the sampling plate and the measurement device.

Preferred features of one aspect of the present invention are also preferred features of any other aspect.

BRIEF DESCRIPTION OF THE DRAWINGS

For a better understanding of the invention, and to show how embodiments of the same may be carried into effect, reference will now be made, by way of example, to the accompanying diagrammatic drawings in which:

FIGS. 3a-3d show a second embodiment of sampling plate at different stages of filling by blood;

FIG. 8aa is an exploded side elevation of the sample measurement system of FIG. 8a;

FIG. 8bb is an exploded side elevation of the sample measurement system of FIG. 8b;

FIG. 8c is an exploded perspective view of a sample measurement system according to another exemplary embodiment;

FIG. 8cc is an exploded side elevation of the sample measurement system of FIG. 8c;

FIG. 8d is a circuit diagram showing the internal components of the adaptor of FIG. 8b;

FIG. 11 is an expanded flow diagram of Step 2 of FIG. 9;
FIG. 12 is an expanded flow diagram of Step 3 of FIG. 9.

DETAILED DESCRIPTION OF THE EXEMPLARY EMBODIMENTS OF THE INVENTION

The exemplary embodiments of the present invention will be discussed in detail in relation to a sampling plate which provides improved spreading of a liquid sample within a sample zone of the sampling plate. In the embodiments discussed below, the sampling plate is for sampling blood to enable the taking of measurements of blood glucose levels in a diabetes patient. However, the teachings, principles and techniques of the present invention are also applicable in other exemplary embodiments. For example, embodiments of the present invention are also applicable to other sampling devices where thorough or selective spreading of a liquid sample is important.

Figure 1:
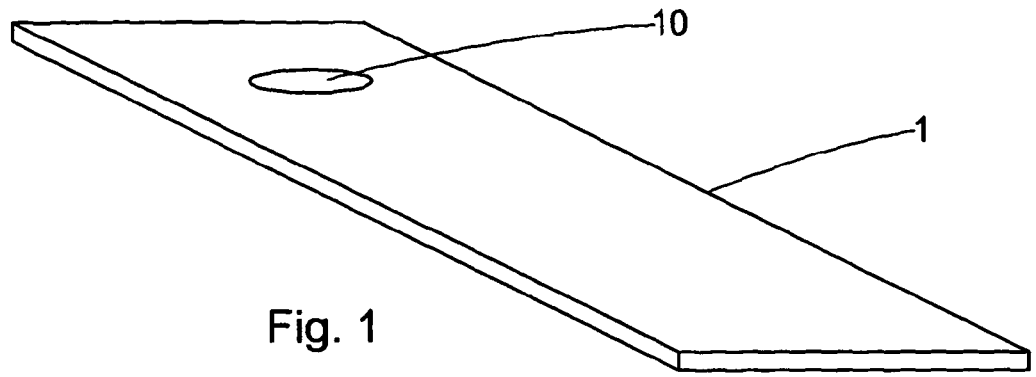
FIG. 1 is an overhead perspective view of a sampling plate relating to an embodiment of the present invention.

FIG. 1 shows a basic sampling plate 1 with a loading port 10 which allows a liquid sample, in this case a blood sample, to be introduced to the sampling plate.

Figure 2:
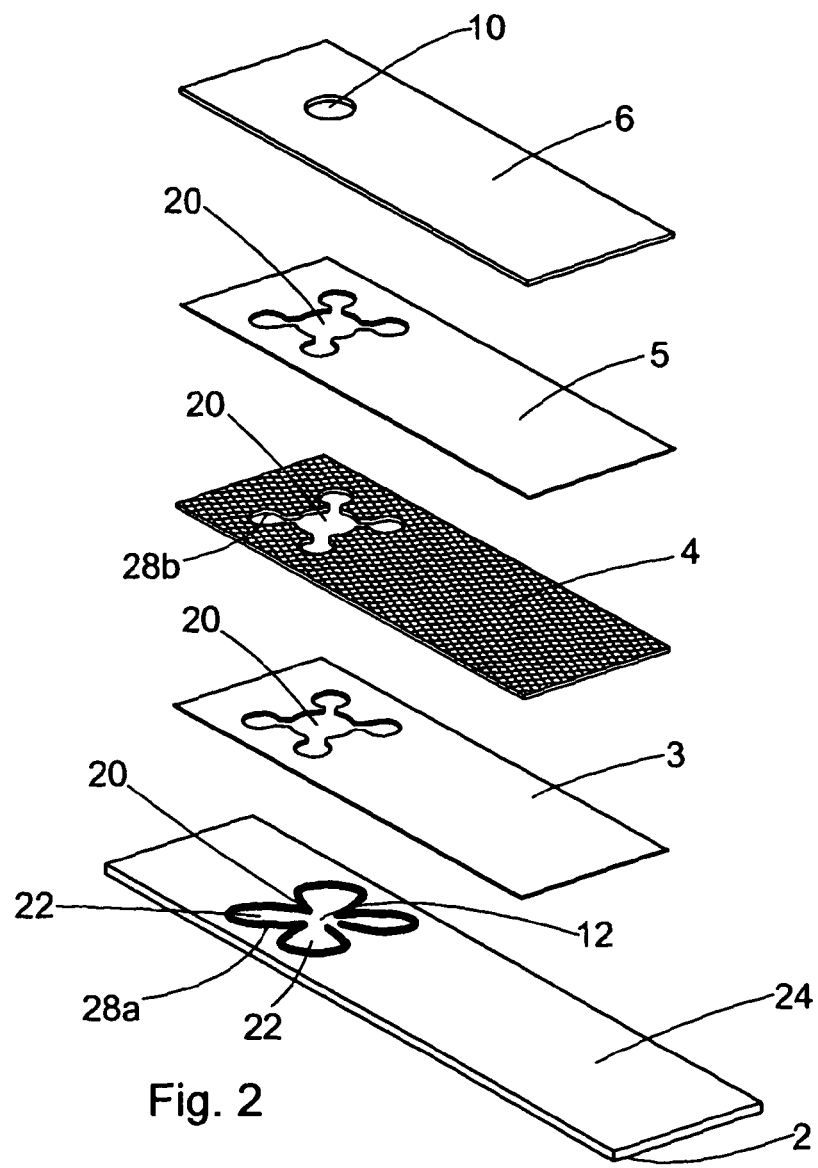
FIG. 2 is an exploded perspective view of various layers of the sampling plate of FIG. 1.

FIG. 2 shows an exploded perspective view of the sampling plate 1 split into the various layers of which the sampling plate 1 is composed, which includes a base plate 2, a first layer of double-sided adhesive tape 3, a layer of hydrophobic mesh 4, a second layer of double-sided adhesive tape 5, and a top layer of hydrophilic film 6.

The base plate 2 has a generally hydrophilic base surface 24 by virtue of a hydrophilic coating of a water-based acrylic polymer and a TWEEN 20 surfactant. The base plate 2 has a sample zone 20. The hydrophobic loading platform has a hydrophobic coating of a hydrophobic acrylic resin, a silicone anti-foaming agent, micronized wax, and fumed silica. Surrounding the loading platform 12 are four testing zones 22, each of which lie on a surface lying beneath the level of the loading platform 12. The four testing zones 22 have respective surfaces which consist of the same hydrophilic material as the hydrophilic base surface 24. The perimeter of the testing zones 22 is defined by a printed hydrophobic ink boundary 28a, composed of the same hydrophobic coating material as above which ensures the blood sample is full contained within the sample zone 20. Lying centrally between the testing zones 22 is a raised loading platform 12 which first receives the blood sample introduced through the loading port 10. The loading platform 12 not only partitions and supplies a received blood sample to the testing zones 22, but also divides the testing zones into discrete testing zones so that an individual blood sample contained within one of the testing zones 22 is completely discrete and separate from other individual blood samples in the other testing zones 22.

The first double-sided adhesive tape 3 is adhered to the top of the base plate 2. The adhesive tape 3 has a cut-out sample zone 20 region so that the sample zone 20 on the base plate 2 is exposed and uncovered. The adhesive tape 3 is made of a non-porous polyester layer coated with synthetic rubber adhesive.

To the upper surface of the double-sided adhesive tape 3 is adhered a hydrophobic mesh 4. The hydrophobic mesh also has a cut-out sample zone 20 region (i.e. an empty portion) to leave the sample zone 20 on the base plate 2 exposed. The internal edge of the cut-out region provides a hydrophobic boundary 28b to the sample zone 20, particularly to the testing zones 22 (in addition to the printed hydrophobic boundary 28a). The hydrophobic mesh 4 is an air porous body in that it is porous to air. The hydrophobic mesh 4 is, however, completely impermeable to the blood sample, thereby allowing the inside edges of the cut-out region of the hydrophobic mesh 4 to entirely contain the blood sample.

The second double-side adhesive tape 5 is identical to the first 3, and is adhered to the top of the hydrophobic mesh 4.

The hydrophobic mesh 4 may be incorporated into a preformed cover tape which is itself composed of numerous layers, including the following:

Layer 1—25 gsm (grams per square meter) of synthetic rubber adhesive.

Layer 2—12 micron thick clear polyester (carrier).
Layer 3—10 gsm of synthetic rubber adhesive.
Layer 4—140 micron thick mesh material 4 (available as Sefar™ Product Code: 07-120 34).
Layer 5—10 gsm of synthetic rubber adhesive.
Layer 6—12 micron thick clear polyester (carrier).
Layer 7—25 gsm of synthetic rubber adhesive.

The mesh material (i.e. Layer 4) is composed of polyester (PET) and is formed as a woven mesh from individual strands of thread. These threads are partially melted together to provide stability and structure to the mesh. The mesh material is then coated with the above mentioned hydrophobic coating. The hydrophobic coating coats all surfaces of the mesh, including inside the pores. Layers 1-3 are the first double-sided adhesive tape 3 and layers 5-7 are the second double-sided adhesive tape 5. The mesh material is an air porous body with an average pore size of 120 microns, a thread diameter of 88 microns, and an average void space (i.e. porosity) of 34%.

The final top layer 6, which is adhered to the top of the second double-sided adhesive tape 5, is a hydrophilic film having a single 3 mm diameter cut-out hole which corresponds to the loading port. When all the layers are adhered together, the loading port is directly above the hydrophobic loading platform 12 which remains exposed and uncovered. The top layer 6 does, however, cover all remain parts of the sample zone 20.

In use, a blood sample applied to the loading port 10 flows downwards under gravity onto the hydrophobic platform 12. From the hydrophobic platform 12 the blood sample spreads into the testing zones 22 in a substantially uniform manner, assisted by the hydrophobic mesh 4 which, by being air porous, readily receives displaced air from the testing zones 22 as the blood sample flows thereinto. When the blood sample reaches the hydrophobic boundary 28, be it formed from the internal edges 28b of the hydrophobic mesh 4 or the printed hydrophobic boundary 28a, it is contained within the boundary 28. The hydrophobic mesh 4 is completely impermeable to the blood sample and is only permeable to air.

FIGS. 3a-3d show an end-fill sampling plate for testing of a single blood droplet, with a volume of approximately 3 μl (though able to handle a reasonable latitude of node, in the form of a blood volumes). There is a sample application point 50 at the end of the strip, leading to a node, which serves as a sample distribution centre 52. In a cruciform arrangement about the sample distribution centre there are four delivery tracks 60; leading to four sensor regions 54, 54', 54" and 54'" in which discrete blood volumes, each of which can be subjected to measurements, independently of the other volumes. Forwards of the sample distribution centre is a separator reservoir 56. The passageway from the sample distribution centre 52 to the separator reservoir 56 is via a narrow neck 58. Passageways to the sensor regions 54 are hydrophobic in character, so that blood flowing into the strip can wash through these passageways, despite their hydrophobic character, but are inhibited from leaving the sensor regions, by flow in the opposite direction. The arrangement is similar to that described in FIGS. 1 and 2.

In the sequence shown in FIGS. 3a to 3d, FIG. 3a shows the strip before blood is delivered to the sample application point. In FIG. 3b the blood has been applied to the sample application point and is being drawn inwards. The blood is indicated by shading 62. Blood is drawn into the sample distribution centre and thence into four delivery tracks 60, and the four sample zones. This state is shown in FIG. 3c. The air displaced by the application of the blood and the subsequent advancement of the sample is accommodated or released by surrounding body 64 which is porous to air but impermeable to blood. Once the delivery tracks 60 and sensor regions 54 are all filled the separator reservoir 56 starts to draw away the excess blood, from the sample distribution centre, and from the delivery tracks 60, leaving the four discrete, separated sub-samples. This state is shown in FIG. 3d. Again, air to be displaced, now from the reservoir, may be released into air porous body around it.

A sample measurement system is now described in which the principles outlined above in relation to the sampling plates described above are applicable.

Figure 4:
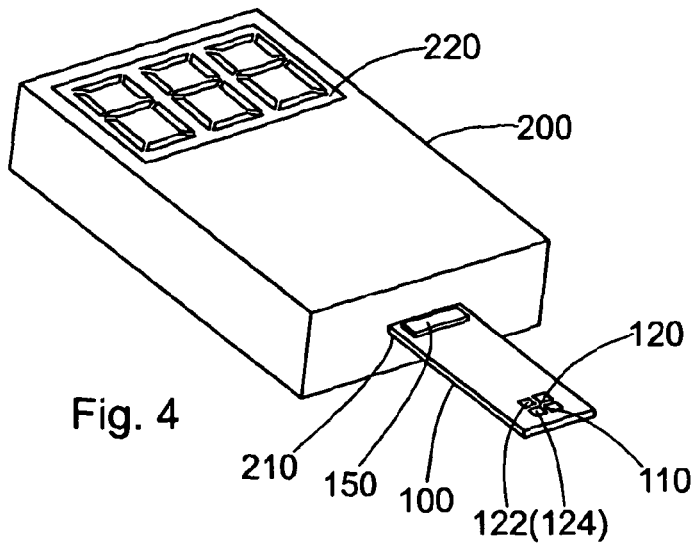
FIG. 4 is a projection view of a sample measurement system according to an exemplary embodiment.

FIG. 4 is a projection view of a sample measurement system according to an exemplary embodiment, and shows a sampling plate 100, based on the multilayered sampling plate 1 of FIGS. 1 to 4, inserted into a measurement device 200. The sampling plate 100 has a loading port 110 for receiving a blood sample on a top face of the sampling plate 100. Directly below the loading port 110 is a sample zone 120 having four discrete testing zones 122, which in this example are three dimensional wells 122. Each well 122 is 250 μm deep, is 1.5 mm wide, and 1.5 mm long. In this example, each of the four wells 122 contains an ink 124. Three of the wells contain an active ink along with a mediator ink. The mediator helps conductivity, and the active ink contains a test material selected for its reactivity with glucose in the blood. In this example, the active ink contains glucose dehydrogenase. The remaining well contains a passive ink along with the mediator ink, where the passive ink is identical to the active ink but without the glucose dehydrogenase. In another embodiment at least one of the wells is spiked with a known quantity of glucose. This assists calibration when conducting measurements. The measurement device 200 has a plate port 210 into which the sampling plate 100 is inserted, and a screen 220 for displaying results, measurements, and/or other desirable data.

In an alternative embodiment the wells 122 are hemispherical. The curved nature of the hemispherical wells is advantageous in that there is a lower risk of the dried inks (in this case flexographically printed conductive inks) cracking than where there are sharp corners such as in rectangular or square wells. In this example, the hemispherical wells (or dimples) have a depth of 150 μm.

Furthermore, the sampling plate 100 has a performance indicator 150. The performance indicator 150 contains information about the sampling plate which, in this example, is transmittable to the measurement device 200. The measurement device 200 has a performance indicator reader (not shown) which reads the information from the performance indicator 150. In this example the performance indicator 150 is an RFID tag which transmits calibration data to the performance indicator reader (a radio frequency receiver). The calibration data relates to the quality of the sampling plate ("performance bands"), for which there can be variation from batch-to-batch or intra-batch. The measurement device 200 then automatically corrects measurements based on the calibration data received to ensure that measurements are consistent from plate to plate, regardless of batch/intra-batch variation.

The performance indicator 150 additionally contains product authentication information to prevent against harmful circulation/use of counterfeit sampling plates. The authentication information is in the form of an encrypted code which can be verified and validated by the measurement device 200.

The performance indicator 150 contains batch information pertaining to the specific sampling plate. The batch information includes a master batch number which refers to the relevant batch records for that particular sampling plate. This renders each sampling plate traceable back to its source materials and production.

The measurement device 200 has a random access memory (RAM) for storing both information from the performance indicators 150 and information/results generated during blood tests. The stored performance indicator information is automatically linked to the corresponding blood test information/results for any particular sampling plate/test.

Blood test results include: measurements, units of measurements, time and date, and also additional information inputted by a patient, including whether a test was performed before or after a meal, before or after exercise, medication type, and quantities. Test results stored within the memory are accessible to allow for a historical analysis of the test results. The information stored in the memory is easily transferable to a computer by linking the measurement device 200 to a computer. In this example, the computer is arranged to assemble a database from the test results to allow a patient's care regime to be carefully monitored.

In this example the memory (RAM) is split into visible and invisible memory, where the visible memory is readily accessible as described above. The invisible memory is only accessible to technicians trained in how to interrogate the measurement device 200. The invisible memory stores batch information for each sampling plate used in a test. Each piece of batch information is linked to a respective blood test result. This allows for interrogation of the measurement device to establish if, when and where an error has occurred. If an error has occurred, the batch information can be used to establish whether there was a problem with a batch of sampling plates (by reference to the relevant batch records), or whether the fault resides with the measurement device itself. This allows any faults to be diagnosed and resolved quickly. This is especially true where batch records are electronically accessible.

In this example, the invisible memory also stores information regarding errors generated during tests, including warning messages displayed to the user. System calibration problems are also stored in the invisible memory.

Figure 5:
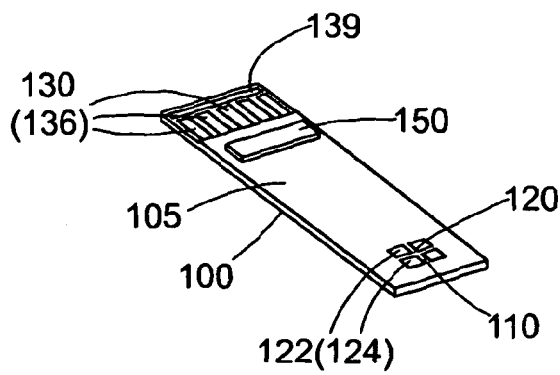
FIG. 5 is a top projection view of a sampling plate according to the exemplary embodiment of FIG. 4.

FIG. 5 is a top projection view of the sampling plate 100, and in addition to FIG. 1 shows a covering tape 105, having an aperture 110 corresponding with the loading port 110, and a series of electrodes 130, the ends (terminal contacts 136) of which connect to electrical terminals within the measurement device 200 to allow measurements to be taken.

Figure 6:
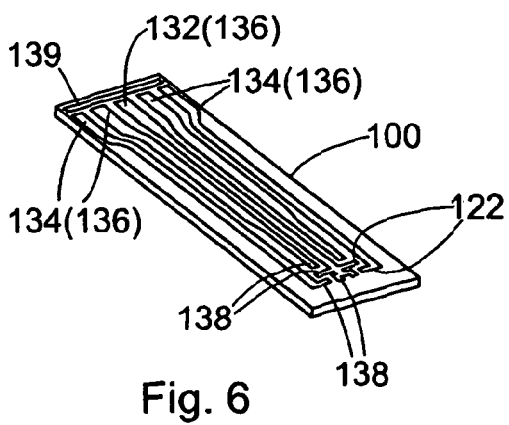
FIG. 6 is a top projection of internal components of the sampling plate of FIG. 5.

FIG. 6 is a top projection of internal components of the sampling plate, and shows the electrodes 130 which, in this example, are formed as a printed circuit board upon a base plate 2 (see FIG. 2). There is a central single common electrode 132 common to all four wells 122. Four individual electrodes 134 join each well. In this example the common electrode 132 is a cathode, and the four individual electrodes 134 are anodes. Each electrode has a terminal contact 136, and an electrolyte contact 138. Each well 122 bridges a gap between each pair of electrodes 130, specifically between a pair of electrolyte contacts 138, where each pair consists of the common electrode 132 and an individual electrode 134. When an electrolyte is present in any of the four wells 122, a current can flow through its corresponding pair of electrodes 132, 134 when the sampling plate 100 is inserted into the measurement device 200 and the measurement device 200 is operated. In this example a four-channel circuit may be produced, enabling four sets of electrochemical measurements on a single sampling plate. The terminals within the measurement device 200 provide a potential difference (voltage) of between 400 and 500 mV. The measured current (microamps) is then proportional to the concentration of glucose within a given blood sample. The sampling plate 100 also comprises a electrical switch bar 139, which acts as a switch to turn on the measurement device 200 when the sampling plate 100 is inserted thereinto.

Figure 7:
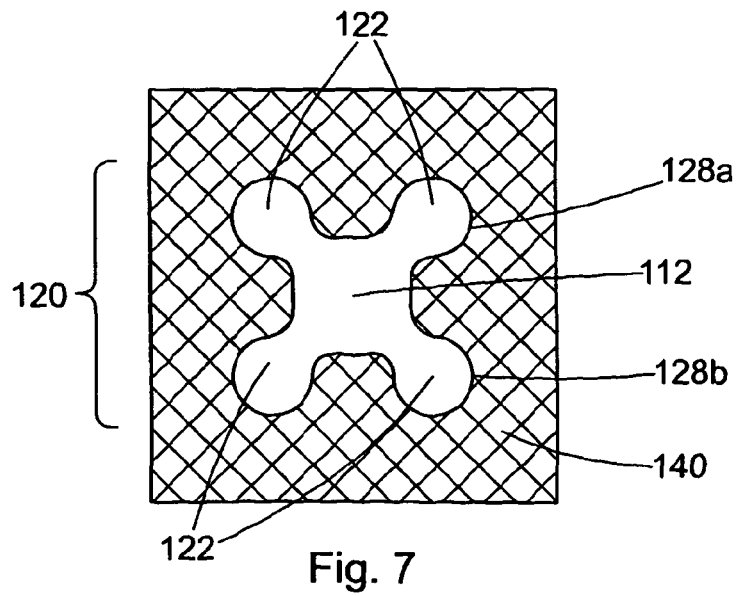
FIG. 7 is a top view of a sample zone of the sampling plate of FIG. 5.

FIG. 7 is a top view of the sample zone 120 of the sampling plate 100 and its surrounding hydrophobic mesh 140. The sample zone 120 is much as described in relation to the sample zone 20 of FIGS. 1 to 2 in that it has wells 122 of hydrophilic material, each well 122 being separated from each other well 122 by a hydrophobic boundary 128 comprised of the printed hydrophobic ink boundary 128a, internal edges 128b of the hydrophobic mesh 140, and the hydrophobic loading platform 112 (in this case the loading platform 112 is the central crossing point of the printed hydrophobic ink boundaries 128a).

Figure 8A:
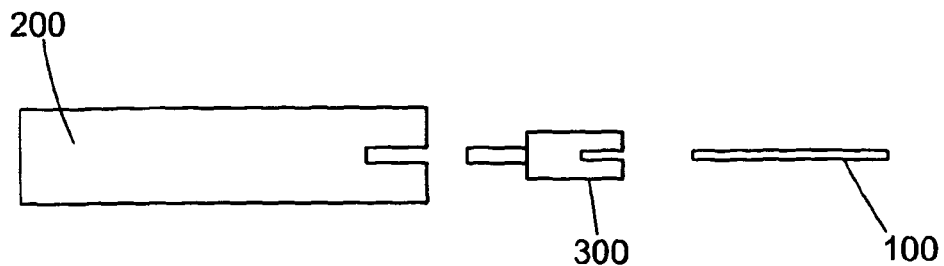
FIG. 8a is an exploded perspective view of a sample measurement system according to another exemplary embodiment.
Figure 8A:
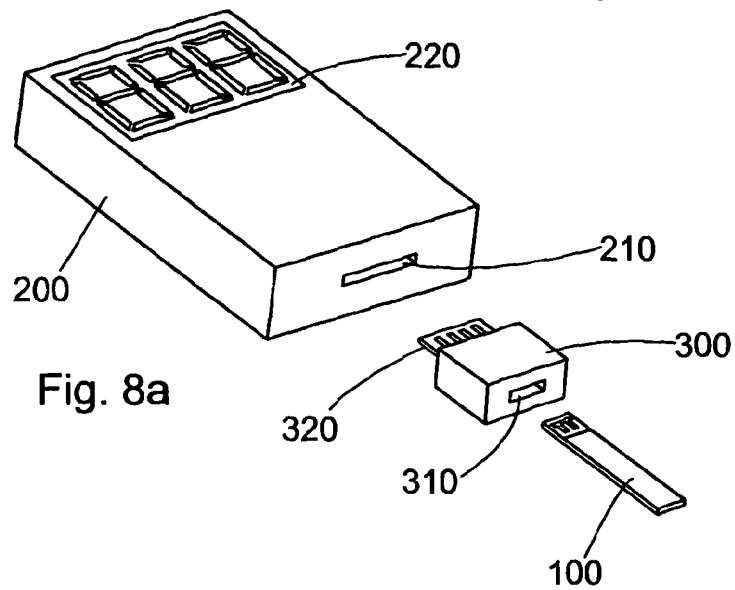
Figure 8B:
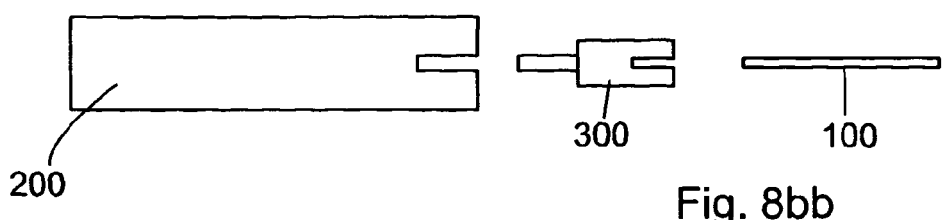
FIG. 8b is an exploded perspective view of a sample measurement system according to another exemplary embodiment.
Figure 8B:
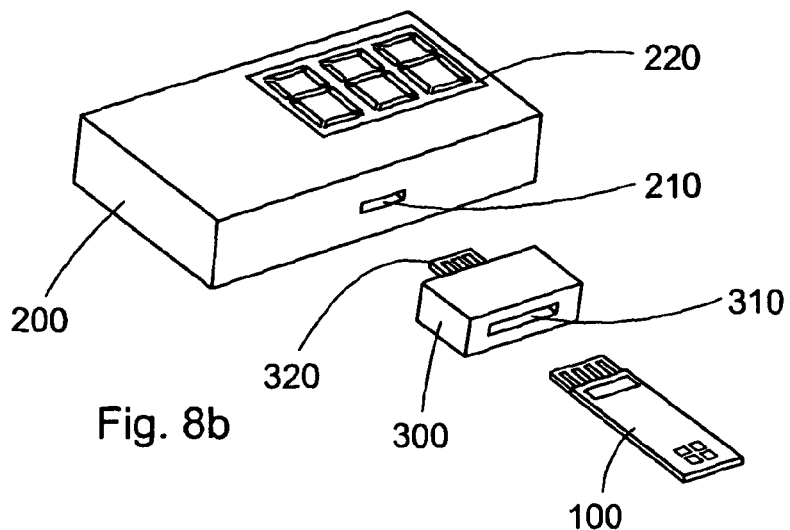

FIGS. 8a, 8b, and 8c are projection views of a sample measurement system according to alternative exemplary embodiments. In each case, a sampling plate 100 is connected to a measurement device 200 via an adaptor 300. In each case, the sampling plate is not directly compatible with the measurement device (i.e. not designed to fit directly into the plate port 210). The adaptor 300 has a plate end 310 (or plate insertion end) designed to receive the sampling plate 100. The plate end 310 has electrical contacts which receive and connect with the terminal contacts 136 of the sampling plate electrodes 130. The adaptor 300 has a device end 320 arranged to simulate a sampling plate which fits directly into the measurement device, and therefore has electrical contacts (pins) arranged to link the electrodes 130 of the sampling plate 100 to corresponding electrical terminals within the measurement device 200. Within the adaptor is a processor which manages the two-way communication between the sampling plate 100 and the measurement device 200. Embodiments of the adaptor 300 enable compatibility between various sampling plates 100 and measurement devices 200. FIG. 8a shows the measurement device 200 of the embodiment of FIG. 4 adapted to receive an otherwise incompatible sampling plate 100. FIG. 8b shows the sampling plate 100 of the embodiment of FIGS. 4 to 7 adapted to fit into an otherwise incompatible measurement device 200. FIG. 8c shows a sampling plate 100 (not of the previous embodiment) adapted to fit into an otherwise incompatible measurement device (not of the previous embodiment).

It will be understood that where the measurement device 200 is a traditional device or other device not arranged or adapted in accordance with the invention, such a device 200 will not have a performance indicator reader, but may still be capable of providing accurate measurements from the sampling plate 100 where the "performance band" is inputted manually into the measurement device.

FIG. 8d shows a circuit diagram of the components within the adaptor 300 of FIG. 8b. The electrodes 130 of the sampling plate 100, as illustrated in FIGS. 3 to 6 interface with the adaptor 300 at contacts at the plate end 310, and are connected by printed circuitry to electrodes 340 at the device end 320. The central single common electrode 132 is directly electrically connected to a primary electrode 342 at the device end 320. In this example, both of these electrodes are cathodes. The four individual electrodes 134 (anodes) connect to two secondary electrodes 344, at the device end 320, via a signal manipulator which, in this example, is a computer processor 350. The processor 350 manipulates four independent signals from the sampling plate 100 to produce two signals that are compatible with the traditional measurement device's hardware and calibration software. Signals $I_1$ and $I_2$ become $I_{U1}$, and signals $I_3$ and $I_4$ become $I_{U2}$.

Figure 8E:
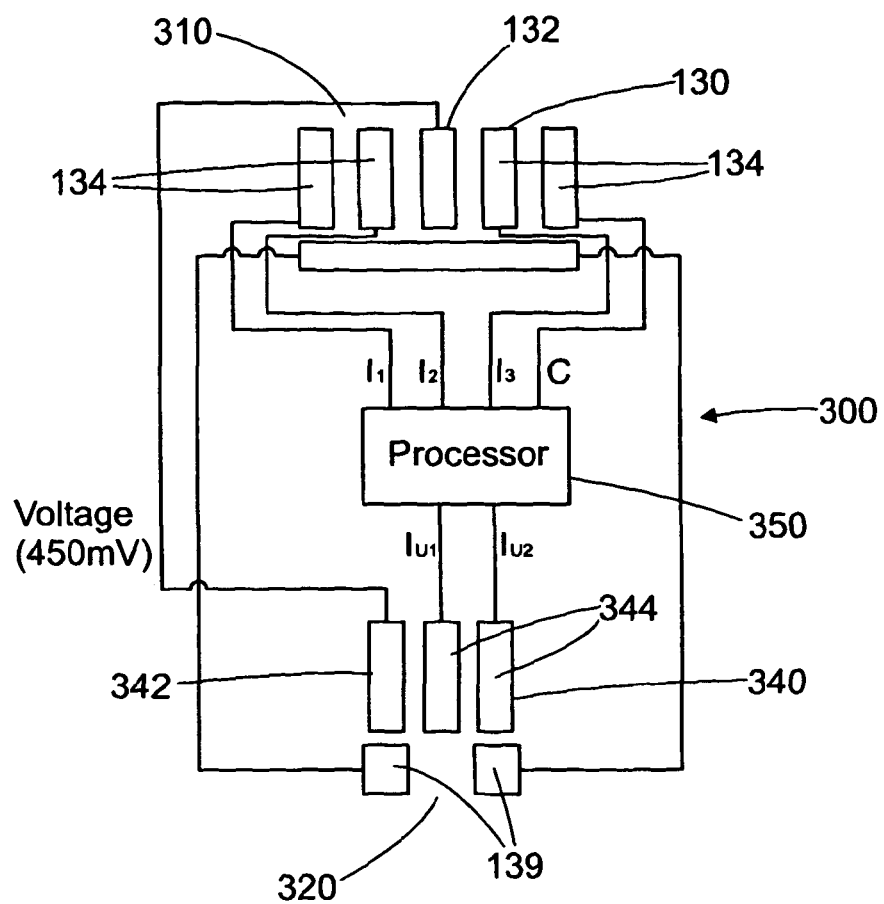
FIG. 8e is a circuit diagram showing the internal components of an alternative adaptor of FIG. 8b.

FIG. 8e shows an alternative arrangement whereby the sampling plate 100 employs three of the anodes 134 ($I_1, I_2, I_3$) for sample measurements, and one of the anodes 134 (C) for correction measurements. In this case, three of the currents ($I_1, I_2, I_3$) are generated through an enzymatic reaction, as discussed above, but a fourth current (C) represents a background signal, which is used for correction. The processor performs a first calculation to generate three corrected glucose signals from the three signals $I_1$, $I_2$, and $I_3$, and also signal C. In this example, the measurement device 200 needs to receive two input signals to make blood glucose measurements. Therefore the processor then manipulates the three corrected signals to produce two signals, $I_{U1}$ and $I_{U2}$, which are compatible with the particular measurement device 200.

As shown in FIG. 8b, the adaptor 300 fits into the plate port 210 by virtue of the device end 320. The device end 320 simulates almost entirely the electrical contacts of otherwise directly compatible sampling plates, except the electrical switch bar 139 is divided into two separate terminals, which connect only when a sampling plate 100 is inserted into the plate end 310 of the adaptor 300. This prevents the measurement device 200 switching on when the adaptor 300 is inserted without a sampling plate 100.

The measurement device 200 of either embodiment of FIG. 4 or 8a-8c has a data carrier containing software. The data carrier may also receive and store data, such as measurements. The measurement device 200 operates pursuant to the software. The software has a default setting which takes current (microamps) measurements from three of the four channels. In this example, the measurement device 200 uses multiplexing to measure each of the four channels separately and sequentially. In other examples measurements from all four channels are taken simultaneously. "Multiplexing" is where a cycle of pulse measurements are taken from each channel in turn before repeating the cycle. In this case, multiplexing occurs at approximately 50 Hz. The data is processed and the results are displayed on the screen 220. In this example the results are indicative of blood glucose levels. Results may be displayed as raw data, or as "high", "low", etc. Messages relating to the new test result and how it compares to the patient's personal parameters will be displayed.

Measurement devices 200 applicable to the present invention are well described in WO 2008/029110, along with their operation.

The measurement device 200 according to the embodiments of both FIGS. 4 and 8 can interface with an ordinary personal computer to allow the raw data to be processed in a customised manner. This furthermore allows unique presentation of the results. The device 200 is simply connectable to a computer as a standard external disc drive.

The sample measurement systems described above are simple to use. The following procedure is employed:
1. The diabetic patient inserts a new test strip 100 into the plate port 210.
2. The measurement device 200 then prepares for receiving measurements and conducts system checks (approximately 3 seconds).
3. The device 200 requests the patient to apply a blood sample to the sampling plate 100.
4. The patient applies a blood sample to the sampling plate 100 via the loading port 110.
5. The device 200 takes measurements for approximately 5 to 10 seconds.
6. The device performs calculations, statistical manipulations, and displays measurement results and accuracy levels.
7. The measurement results and accuracy levels are stored in the device's 200 memory.

In this example the device 200 switches on as soon as the plate 100 is inserted into the port 210, by virtue of the switch bar 139. During step 4, the sampling plate 100 automatically separates the blood into the four discrete wells 122. The hydrophobic mesh 140 encourages uniform spreading of blood across the sample zone, by providing ventilation for the air being displaced, such that blood sample enters the wells 122 under the influence of both gravity and the hydrophilic attraction provided by the hydrophilic surface of the wells 122. Blood does not spread beyond the hydrophobic boundary 128, particularly as the mesh 140 is entirely impermeable to blood.

The device 200 processes the measurements in view of the calibration data from the RFID tag 150, and also internally calibrates and/or performs accuracy level calculations from the measurements taken from each of the wells 122. Internal calibration is effected by the use of statistical algorithms based on the inks and components of the blood which are the subject of measurement. Statistical algorithms are also used to establish the accuracy level of the measurements taken. The screen 220 then displays the result either as raw data, such as blood sugar concentration, or as "high" or "low", depending on the user's preference. The device 200 also displays the accuracy level. Messages relating to the new test result and how it compares to the patient's personal parameters will be displayed.

Results are calculated on the basis of current decay across a particular well as measured over 5 to 10 seconds. The rate of decay provides an indication of blood glucose levels.

In this example the measurement device 200 also displays, on the screen 220, an accuracy level or an error message if the accuracy level is outside a predefined range. Regulation dictates that blood glucose measurement systems must provide test results with a minimum accuracy level. Thus the predefined range will always comply with regulatory standards. Thus any results with an accuracy outside these limits will give rise to an error message, indicating that the test should be repeated.

In this example, the sampling plates 100 are produced as follows.

Figure 9:
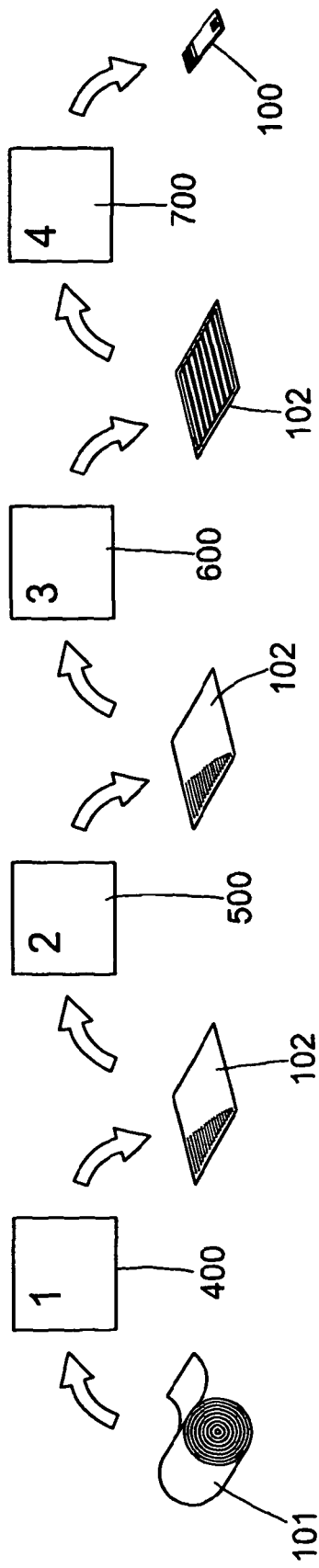
FIG. 9 is a flow diagram overview of the method of producing a sampling plate.

FIG. 9 is a flow diagram overview of a method of producing a sampling plate from a continuous sheet. The diagram shows the method being carried out at four processing stations, including:
Step 1: A flexographic printing station 400;
Step 2: A precision dosing station 500;
Step 3: A card finishing station 600; and
Step 4: A strip cutting and vialing station 700.

A continuous sheet in the form of a continuous roll is fed into the flexographic printing station 400. In this example, the continuous sheet is calendered cardboard. It is calandered to provide the sheet with a greater level of uniformity to reduce variations in the strips ultimately produced. In this example, the continuous sheet is also supplied with a surface that is hydrophilic in nature. Alternatively a hydrophilic coating may be applied at the beginning of the flexographic printing process. The output of step 1 is a smaller continuous sheet, in this example a card having 200 sampling plates (strips), arranged as 8 rows of 25 strips. Inks are then precisely dosed during step 2 at the precision dosing station 500. Step 3 involves finishing the card by applying additional layers at the card finishing station 600. Finally Step 4, at the strip cutting and vialing station 700, involves cutting the card to provide individual strips ready for use and packaging sets of strips in vials.

Figure 10:
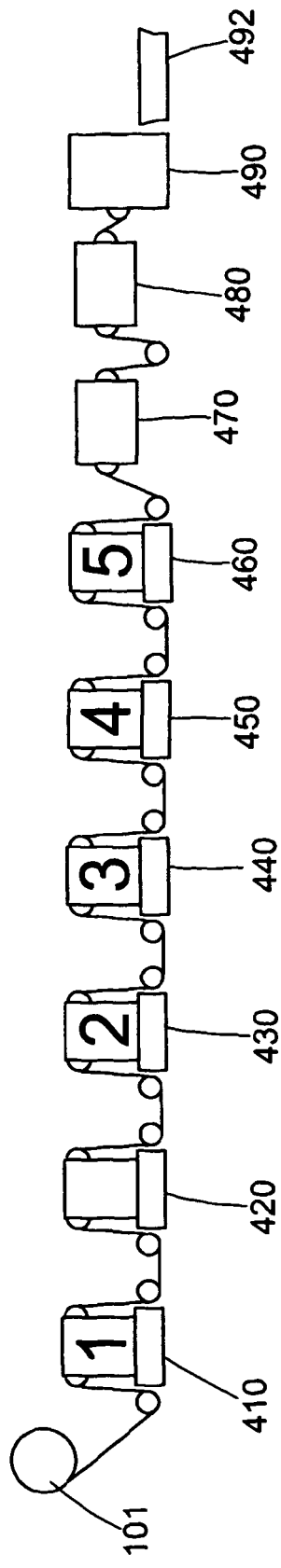
FIG. 10 is an expanded flow diagram of Step 1 of FIG. 9.

FIG. 10 is an expanded flow diagram of Step 1 of FIG. 9, and shows the flexographic printing process at the flexographic printing station 400 in more detail. The flexographic printing station 400 comprises a plurality of in-line flexographic print modules and further process modules. A continuous roll 101 is first fed into a first flexographic print module 410 for printing the electrodes 130 and registration points. There is a registration point at regular intervals along the roll 101. The roll then proceeds to a surface deformation module 420, where four three-dimensional wells 122 are formed, in respect of each strip 100 on the roll, using a roller tool set. The roll then proceeds to a second flexographic print module 430, where the insulation layer is printed over the electrodes, so as to leave terminal contacts 136 and electrolyte contacts 138. The insulation layer is composed of ingredients that do not conduct electrical signals (resin and photo-curing agents), and is applied between the electrodes 130 to minimise signal interference which, for instance, can be induced in neighbouring electrodes if uninsulated. At a third flexographic print module 440, the hydrophobic boundary 128 is printed around the wells 122. At a fourth flexographic print module 450, a first decorative artwork colour is flexographically printed in respect of each strip 100 on the roll 101. At a fifth flexographic print module 460, a second decorative artwork colour is printed. Optionally there may be additional flexographic print modules for printing additional artwork. Such flexographic printing allows for high resolution images small enough to be printed on a sampling plate 100. Such images may provide simple information or alternatively enhance product aesthetics, or include branding etc. The roll then proceeds to an edge trimming module 470, where edges of the roll 101 are trimmed based on the positions of the registration points. The roll then enters a perforating module 480, where accurately aligned micro-perforations are applied to the roll along an edge of each row of strips. Finally the roll enters a card cutting module 490 where the roll is cut to produce a number of cards 102, which are deposited in a first card collector 492. Each card contains two hundred strips (8 rows of 25 strips). The roll 101 proceeds through the flexographic printing station 400 on conveyer rollers 402 until it is cut into cards 102. Each flexographic print module has a flexographic unit and a drier. The printing of an individual layer is accurate to +/−30 micrometers. Print layer on print layer accuracy is +/−50 micrometers. The throughput through the flexographic printing station 400 is generally about 300 meters/min.

In alternative embodiments, there is a surface coating flexographic printing module before the first flexographic printing module 410. The surface coating module applies a surface coating of resin and surfactant which seals the surface so that the roll 101 is less porous and less likely to absorb inks. The surface coating gives the roll 101 a substantially uniform surface energy throughout, and a substantially uniform porosity.

In some embodiments there may be multiple layers of electrode applied so as to increase conductivity. The extra layers are applied on top of the original layer(s). This may be performed at the same flexographic printing module 410, or additional electrode layers may be applied at subsequent printing modules. The electrode inks are composed of resin, surfactant, carbon and graphite.

In an alternative embodiment, the surface deformation module 420 may be the final module after all flexographic inks have been applied. This can help improve the accuracy of the ink application processes.

FIG. 11 is an expanded flow diagram of Step 2 of FIG. 9, and shows the precision dosing process at the precision dosing station 500 in more detail. Here inks are nano-dosed (120 nL+/−5 nL per ink) with volumetric and positional precision, with each well 122 creating an excellent three-dimensional target for each ink. Chemical solutions of the inks are produced, in this example, with ethanol as solvent. A card 102 from Step 1 is first introduced to a first dosing unit 510, where an ink solution containing a mixture of a mediator ink and an active ink is dosed into one well 122 per strip 100 on the card 102. It should be noted that embodiments which use the same ink in more than one well per strip may have each such well dosed with the same ink at the same dosing unit. The card 102 is then dried in a first drying unit 512 The card 102 proceeds to a second dosing unit 520 where another ink solution of mediator/active ink is dosed to another well 122 per strip 100 on the card 102. The card is then again dried in a second drying unit 522. Finally the card 102 proceeds to a third dosing unit 530 where yet another ink solution of mediator/active ink is dosed to a further well 122 per strip 100 on the card 102. The card is then dried in a third drying unit 532 and deposited in a second card collector 540. Optionally a fourth ink solution may be dosed into a further well, which ink solution contains a mediator/passive ink. In this embodiment the active ink contains glucose dehydrogenase. However, in other embodiments the active ink may be different to allow measurements relating to a condition other than diabetes. Alternatively the active inks present may be different from each other to allow simultaneous measurements relating to a plurality of conditions. It is during the precision dosing that different inks may be dosed depending on the measurements ultimately desired. For instance, dosing one ink for measuring glucose levels, and another for measuring ketone levels is easily achievable.

Figure 13:
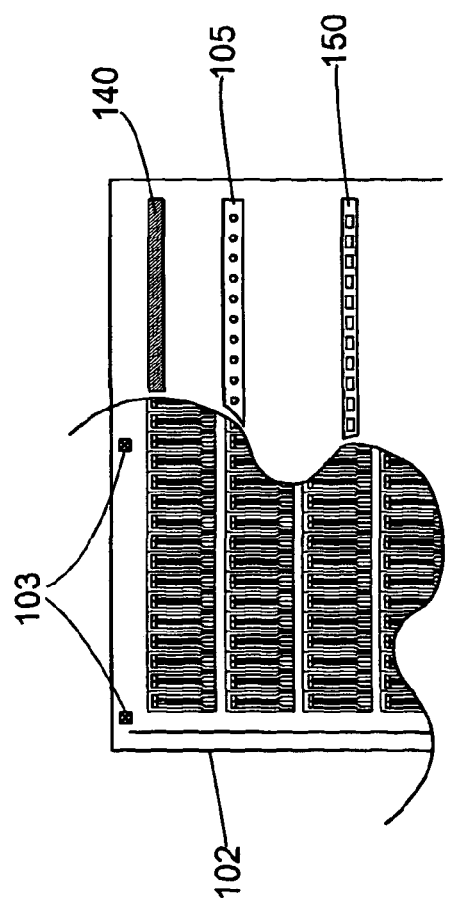
FIG. 13 is a top view of a card produced from Step 3 of FIG. 9.

FIG. 12 is an expanded flow diagram of Step 4 of FIG. 9, and shows the card finishing process at the card finishing station 600 in more detail. FIG. 13 is a top view of a card produced at the card finishing station 600. The card finishing station 600 applies three further materials to the card 102: a hydrophobic mesh 140 (as per the pre-formed cover tape comprising Layers 1-7 of FIG. 2), a covering tape 105 (as per the top layer of hydrophilic film 6 of FIG. 2), and RFID tags 150 (radio-frequency identification strips). FIG. 13 also shows the registration points 103 spaced at regular intervals on the card 102. In Step 3 a card 102 from Step 2 is transferred to a machine bed of the card finishing station 600. In an embodiment which incorporates the mesh 140, the card 102 is conveyed to a mesh-laying unit 610 with a card vision and position system 612. The vision system 612 establishes the precise location of the card 102. The card position system corrects the position of the card relative to the mesh-laying unit 610. The unit 610 places mesh ribbons 140 across the strips 100. A single mesh ribbon 140 is laid along a single row of strips 100 and adhered thereto by virtue of the double-sided adhesive layer attached to the mesh material (see FIG. 2). The mesh ribbons are anchored by ultrasonic welding before they are cut from feed rolls of the mesh ribbon 140. The card 102 is then taken along the machine bed to a hotmelt pattern laying unit 620, where another vision system 622 pinpoints the location of the card before a hotmelt application head moves across the card 102. The card is then conveyed to a covering tape-laying unit 630. Lanes of covering tape 105 are positioned above the mesh ribbons 140 on top of the double-sided adhesive layer on top of the mesh material (see FIG. 2). Another vision system 632 controls roll out of the covering tape 105 so as to correctly align a hole in the tape 105 with the loading port 110 and sample zone 120 of each strip 100. Downward pressure and heat is then applied to secure the covering tapes 105 before they are cut from their respective feed rolls. The card is then conveyed to an RFID ribbon-laying unit 640, where a vision system 642 again controls the positioning of the RFID ribbon 150 and again corrects the card position with a position system before downward pressure is applied to secure the RFID ribbon 150. The RFID ribbon 150 is self-adhesive and is placed near to the terminal contacts 136 at an end of the strip 100 which is connectable to the measurement device 200. Once the RFID ribbons 150 are cut from their feed rolls to leave RFID tags 150 on each strip 100, the card 102 then proceeds to a third card collector 650. At this stage the performance band of the batch of test strips is determined by destructively testing 1% of all finished cards 102 in a testing unit 660. The testing unit applies a precisely dosed glucose solution to each well 122 of a strip 100 taken from a card 102, and takes measurements to obtain a card's 102 performance profile data. This data is uploaded to a production control database and stored as part of a batch record. The data is then recalled in Step 4 (see below). The mesh ribbons 140 are positioned with an accuracy of +/−200 micrometers or better, relative to the registration points on the card 102. The hotmelt pattern is positioned with an accuracy of +/−200 micrometers. The covering tape is positioned with an accuracy of +/−100 micrometers, as is the positioning of the hole in the tape relative to the loading port 110. The RFID ribbons are positioned with an accuracy of +/−200 micrometers.

Figure 14:
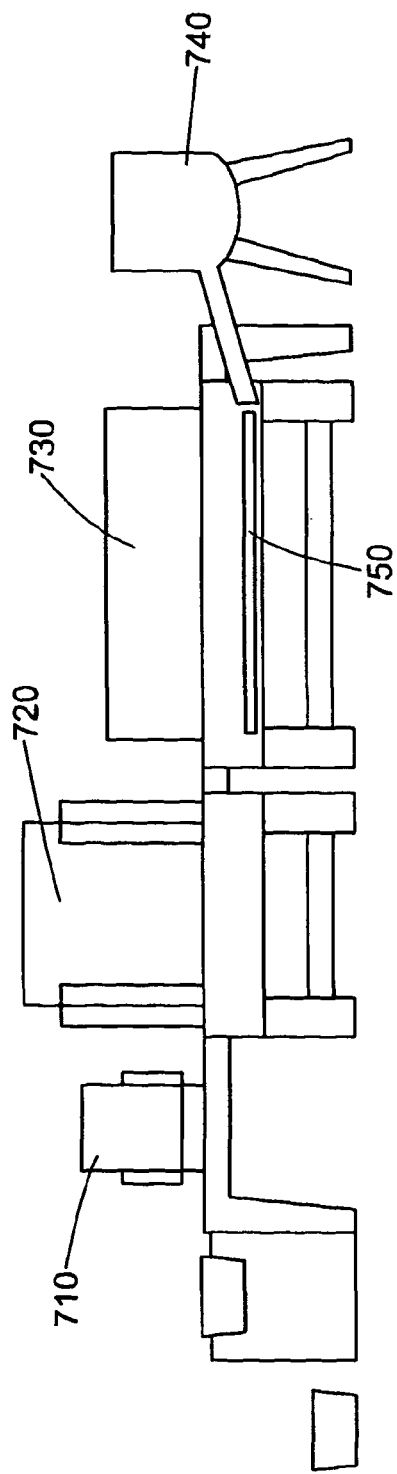
FIG. 14 is an expanded flow diagram of Step 4 of FIG. 9.

FIG. 14 is an expanded flow diagram of Step 5 of FIG. 9, and shows the strip cutting and vialing process at the strip cutting and vialing station 700 in more detail. A finished card 102 is transferred from Step 3 to an input track of the station 700. The card is first taken to an RFID programming unit 710, where each of the RFID tags 150 associated with each strip is programmed by retrieving the performance profile data obtained in Step 3 from the batch record database. The data is imparted to the RFID tags 150 to be later read by the measurement device 200 when a patient inserts a strip 100 thereinto. The programmed card 102 is then taken to a row-cutting unit 720 where each card 102 is divided into 8 separate rows along the perforations. Such perforations help the accuracy of cutting, and therefore reduce the space needed between rows, thereby increasing the number of sampling plates per square meter. Wear and tear of the cutter is also reduced. Each card 102 has a waste area at either end. This waste area is removed as part of the row-cutting process and the waste is collected for disposal. The separated rows are collected and transferred to a strip cutting unit 730 where lasers (or alternatively knives) are used to convert each row into 25 individual strips 100. Each row has an area of waste material at each end, which is suitably removed and disposed of at the strip cutting unit 730. Closed vials are then introduced to the cutting and vialing station 700 via a vial hopper 740. Vials are transferred and orientated before being presented for filling. A filling system 750 opens each vial and places up to 25 strips therein before closing the vial. The vials of strips are stored until distribution requests are received. At this point the vials are retrieved and packaged with all necessary labelling, user guides, information, particularly information on performance bands. The strips are then ready for distribution. Row cutting is carried out with an accuracy of +/−100 micrometers. Strip cutting is carried out with an accuracy of +/−100 micrometres.

The original continuous roll 101 is made of paper-based material (i.e. card). In this example the card is coated with a lacquer. Alternatively, however, the roll 101 could be of polymer based materials, such as PVC or polycarbonate.

COMPARATIVE EXAMPLES

Four different sampling plates 1 as per FIGS. 1 to 2 were made and tested in terms of their respective ability to uniformly spread a blood sample throughout the testing zones 22.

Each sampling plate 1 was constructed from a base plate 2 and a multi-layered cover tape 3,4,5,6, where the cover tape 3,4,5,6 was pre-formed as a finished component before being adhered to the base plate 2.

The cover tape 3,4,5,6 was formed by first sandwiching a hydrophobic mesh layer 4 between two double-sided adhesive tapes 3,5 to form a double-sided adhesive mesh 3,4,5. Each double-sided adhesive tape 3,5 consists of a piece of polyester having its entire surface coated with a particular amount of adhesive. A sample zone-shaped hole 20 was then cut out of the double-sided adhesive mesh 3,4,5. A liner was then removed from one of the double-sided adhesive tapes 3,5 and the revealed adhesive surface was adhered to a hydrophilic film 6 having a 3 mm diameter hole to give the cover tape 3,4,5,6. The hydrophilic film 6 was adhered to the double-sided adhesive mesh 3,4,5 such that the 3 mm hole coincided with the centre of the cut-out sample zone region 20. The 3 mm hole thus acted as a loading port 10. A liner was then removed from the other of the double-sided adhesive tapes 3,5 and the revealed adhesive surface was adhered to the base plate 2 such that the centre of the cut-out sample zone 20 region coincided with a raised hydrophobic loading platform 12 upon the base plate 2.

The four sampling plates used as comparative examples were as follows:

1) Comparative Example 1a—the sampling plate 1 as per FIGS. 1 and 2 but the hydrophobic mesh layer 4 was replaced with a non-porous sheet of hydrophilic coated polyester.
2) Comparative Example 2a—the sampling plate 1 as per FIGS. 1 and 2, with a hydrophobic mesh layer 4 of Sefar 07-120 34 polyester, where each of the adhesive tapes 3,5 had 20 g/m$^2$ of adhesive on their respective surfaces.
3) Comparative Example 3a—the sampling plate 1 as per FIGS. 1 and 2, with a hydrophobic mesh layer 4 of Sefar 07-120 34 polyester, where each of the adhesive tapes 3,5 had 15 g/m$^2$ of adhesive on their respective surfaces.
4) Comparative Example 4a—the sampling plate 1 as per FIGS. 1 and 2, with a hydrophobic mesh layer 4 of Sefar 07-120 34 polyester, where each of the adhesive tapes 3,5 had 10 g/m$^2$ of adhesive on their respective surfaces.

In each comparative example a 10 μl blood sample was loaded to the sample zone 20 via the loading port 10 and the sampling plate 1 left for 30 seconds before the top layer of hydrophilic film 6 was removed to allow visual inspection of the sample zone. Spreading efficiency in each case was then measured by visual inspection. The results are provided in Table 1 below, where spreading efficiency was considered to be either very poor, poor, medium, good, or very good, based on the following criteria:

Total spreading (i.e. coverage of the testing zones)
Air pocket formation
Bias towards filling only certain testing zones and not others.

TABLE 1

| Comparative Example | Spreading Efficiency | Comments |
| --- | --- | --- |
| 1a | Very poor | Blood only entered 2 testing zones and left the other two empty - air pockets were formed in testing zones where blood present. |
| 2a | Poor | Some blood sample entered each of the 4 testing zones but was not spread homogeneously. Air pockets were evident. Adhesive seemed to block the mesh pores. |
| 3a | Medium | Blood sample entered each of the 4 testing zones but air pockets were evident in some |

TABLE 1-continued

| Comparative Example | Spreading Efficiency | Comments |
|---|---|---|
| | | of the testing zones. Adhesive seemed to partially block the mesh pores. |
| 4a | Very good | Spread homogeneously throughout all testing zones - no air pockets. |

These comparative examples clearly demonstrate the effect of an air porous body on sample spreading. The worst performer, comparative example 1a, had no porous mesh. The second worst, comparative example 2a, had the same porous mesh as comparative examples 3a and 4a, but the high levels of adhesive caused blockage of the mesh pores, thus preventing the mesh from effectively ventilating air. The second best, comparative example 3a, again suffered from partial blocking of the mesh pores. Finally, comparative example 4a with its low levels of adhesive, allowed for excellent spreading efficiency due to minimal blockage of the mesh pores. Comparative example 4a was the only example in which the blood sample was completely separated into discrete samples within the testing zones so that no samples were linked via blood creating a fluid path across the hydrophobic loading platform 12. The hydrophobic boundaries 128 prevented the blood samples from remerging.

The above tests were repeated in respect of all the four comparative examples, only this time no hydrophilic film 6 was present on the cover tape 3,4,5. This allowed visual inspection of spreading rates. As such comparative examples 1b, 2b, 3b, and 4b correspond to examples 1a-4a without hydrophilic films.

In each comparative example a 10 μl blood sample was loaded to the sample zone 20 via the hydrophobic loading platform 12 which was clearly visible and accessible through the cut-out region of the sample zone 20. Spreading dynamics and rates were then visually observed and recorded. Results are presented in Table 2 below.

TABLE 2

| Comparative Example | Spreading Efficiency | Comments |
|---|---|---|
| 1b | Very poor | Blood only entered 2 testing zones and left the other two empty - air pockets were formed in testing zones where blood present. The spreading that happened occurred relatively slowly and ceased before providing any discrete samples - samples in testing zones were linked via blood over the loading platform. |
| 2b | Poor | Some blood sample entered each of the 4 testing zones but was not spread homogeneously. Air pockets were evident. Adhesive seemed to block the mesh pores. The spreading that happened occurred quite quickly but ceased before providing totally discrete samples - most samples in testing zones were linked via blood over the loading platform. |
| 3b | Medium | Blood sample entered each of the 4 testing zones but air pockets were evident in some of the testing zones. Adhesive seemed to partially block the mesh pores. The spreading that happened occurred very quickly but ceased before providing four discrete samples - 2 of the testing zone samples were linked via blood over the loading platform. |
| 4b | Very good | Spread homogeneously throughout all testing zones - no air pockets. The spreading that happened occurred very quickly and provided four completely discrete samples. |

TABLE 2-continued

| Comparative Example | Spreading Efficiency | Comments |
|---|---|---|
| | | spreading that happened occurred very quickly and provided four completely discrete samples. |

Table 2 clearly demonstrates the effect of the air porous body on spreading rates and the ability to obtain totally discrete samples for a given volume of the sample zone and a given volume of blood sample.

The invention claimed is:

1. A sampling plate, comprising:
a sample zone for receiving a liquid sample, the sample zone comprising at least two discrete testing zones and a separation means comprising a hydrophobic zone for separating the liquid sample into at least two discrete samples occupying a respective testing zone; and
an air porous body which is in fluid communication with the sample zone;
wherein the air porous body is arranged to receive air displaced from the sample zone as the liquid sample is received into the sample zone.

2. The sampling plate as claimed in claim 1, wherein the air porous body is substantially impermeable to water.

3. The sampling plate as claimed in claim 1, wherein the air porous body is arranged to hold the liquid sample within the sample zone.

4. The sampling plate as claimed in claim 1, wherein the air porous body is located substantially around the perimeter of the sample zone.

5. The sampling plate as claimed in claim 1, wherein the air porous body comprises hydrophobic material.

6. The sampling plate as claimed in claim 1, wherein the air porous body has a porosity of 0.2 or more.

7. The sampling plate as claimed in claim 1, wherein the air porous body comprises a mesh.

8. The sampling plate as claimed in claim 7 wherein the mesh comprises polyether ether ketone (PEEK), polypropylene (PP), polyester (PET), polyvinylidene fluoride (PVDF), ethylene chlorotrifluoroethylene (ECTFE), ethylene co-tetrafluoroethylene (ETFE), nylon (polyamide), or fluorinated ethylene-propylene (FEP).

9. The sampling plate as claimed in claim 1, wherein the air porous body is a porous layer of the sampling plate, the layer comprising an empty portion arranged to receive and contain the liquid sample.

10. The sampling plate as claimed in claim 1, the sample zone comprises at least one hydrophilic floor for containing the liquid sample.

11. The sampling plate as claimed in claim 1, comprising a loading port located on a top face of the sampling plate.

12. A sampling plate, comprising:
a sample zone for receiving a liquid sample;
an air porous but water impermeable body which is in fluid communication with the sample zone, the air porous body being arranged to receive air displaced from the sample zone as the liquid sample is received into the sample zone;
a loading port for loading the liquid sample; and
a loading path between the loading port and sample zone along which the liquid sample can travel towards the sample zone;

wherein the sample zone comprises:

at least two discrete testing zones, each defined by a well, having a hydrophobic boundary lying between the at least two testing zones; and a raised hydrophobic loading platform located towards a central region lying between all the respective testing zones, the loading platform being arranged to first receive the liquid sample before distributing the liquid sample amongst the respective testing zones;

wherein each testing zone comprises:

a hydrophilic portion; and a pair of electrodes which is bridged, in use, by the liquid sample in a testing zone.

13. A sampling plate, comprising:

a sample zone for receiving a liquid sample;

an air porous body which is in fluid communication with the sample zone; and at least one pair of electrodes arranged to permit an electrochemical measurement to be taken in respect of the liquid sample, wherein the air porous body is arranged to receive air displaced from the sample zone as the liquid sample is received into the sample zone.

* * * * *